United States Patent [19]

Jiminez et al.

[11] 4,434,801
[45] * Mar. 6, 1984

[54] APPARATUS FOR TESTING PHYSICAL CONDITION OF A SELF-PROPELLED VEHICLE RIDER

[75] Inventors: Oscar Jiminez, Miami; Frank J. Bianco, Pembroke Pines, both of Fla.

[73] Assignee: Biotechnology, Inc., Miami, Fla.

[*] Notice: The portion of the term of this patent subsequent to Jan. 11, 2000 has been disclaimed.

[21] Appl. No.: 355,329

[22] Filed: Mar. 8, 1982

Related U.S. Application Data

[63] Continuation-in-part of Ser. No. 145,765, Apr. 30, 1980, Pat. No. 4,367,752.

[51] Int. Cl.³ .............................................. A61B 5/02
[52] U.S. Cl. .................................. 128/689; 128/707; 128/782; 324/166; 280/289 R; 350/99
[58] Field of Search ..................... 33/DIG. 1, 125 R; 46/45; 73/518-520; 116/62.1-62.4; 235/95 R, 104; 272/73, DIG. 6; 280/200, 289 R; 324/166; 350/97, 99; 364/413, 561, 565

[56] References Cited

U.S. PATENT DOCUMENTS

| | | |
|---|---|---|
| 2,382,832 | 8/1945 | Thornton . |
| 3,395,698 | 8/1968 | Morehouse . |
| 3,518,985 | 7/1970 | Quinton . |
| 3,675,199 | 7/1972 | Jamison et al. . |
| 3,675,640 | 7/1972 | Gatts . |
| 3,744,480 | 7/1973 | Gause et al. . |
| 3,781,082 | 12/1973 | Linder ............................. 350/97 X |
| 3,797,010 | 3/1974 | Adler et al. . |
| 3,807,388 | 4/1974 | Orr et al. . |
| 3,898,563 | 8/1975 | Erisman ............................ 324/166 |
| 3,910,257 | 10/1975 | Fletcher et al. . |
| 3,967,879 | 7/1976 | Tsuyama . |
| 3,978,849 | 9/1976 | Geneen . |
| 3,991,747 | 11/1976 | Stanly et al. . |
| 4,007,419 | 2/1977 | Jasmine . |
| 4,019,171 | 4/1977 | Martelet . |
| 4,053,755 | 10/1977 | Sherrill . |
| 4,101,071 | 7/1978 | Brejnik et al. . |
| 4,108,166 | 8/1978 | Schmid . |
| 4,112,928 | 9/1978 | Dutsch . |
| 4,117,834 | 10/1978 | McPartland et al. . |
| 4,144,568 | 3/1979 | Hiller et al. . |
| 4,156,190 | 5/1979 | Chittenden et al. . |
| 4,192,000 | 3/1980 | Lipsey . |
| 4,201,448 | 5/1980 | Kagayama . |
| 4,202,350 | 5/1980 | Walton . |
| 4,216,956 | 8/1980 | Yamamura et al. . |
| 4,220,996 | 9/1980 | Searcy . |
| 4,223,211 | 9/1980 | Allsen et al. . |
| 4,278,095 | 7/1981 | Lapeyre ........................... 128/707 X |
| 4,281,663 | 8/1981 | Pringle . |
| 4,312,358 | 1/1982 | Barney ............................. 128/736 X |
| 4,367,752 | 1/1983 | Jiminez et al. .................. 128/707 X |

OTHER PUBLICATIONS

Mereness, T. S., "Bicycle Tachometer/Speedometer", IBM Technical Disclosure Bulletin, vol. 17, No. 9, Feb. 1975, pp. 2570-2571.

Randig, George W., "Build a Digital Bicycle-Speedometer", Popular Electronics, Mar. 1977, pp. 39-41.

Primary Examiner—Kyle L. Howell
Assistant Examiner—Francis J. Jaworski
Attorney, Agent, or Firm—Lowe, King, Price & Becker

[57] ABSTRACT

The physical condition of a bicycle rider is tested by monitoring the heart beat of the rider and the distance traversed during testing. A portable electronic instrument housing includes a digital computer responsive to signals indicative of the heart beat and travel distance, numerical quantities associated with physiological parameters of the rider, and a clock source to derive signals indicative of different physical activities of the rider. The distance signal is derived by mounting a permanent magnet in a reflector carried by wheel spokes of the bicycle. A first reed switch responds to flux from the permanent magnet to derive a pulse for each wheel revolution. A pulse for each revolution of the bicycle sprocket assembly, derived by a second permanent magnet-reed switch combination, is coupled to the computer and combined with the clock source to derive a signal indicative of number of sprocket assembly turns per unit length of time. A cueing signal to signal the cyclist when he should complete each pedal turn to assist in maintaining a constant forward speed, regardless of gear ratio, is derived by combining the pulses from the two reed switches with a desired forward speed signal.

30 Claims, 11 Drawing Figures

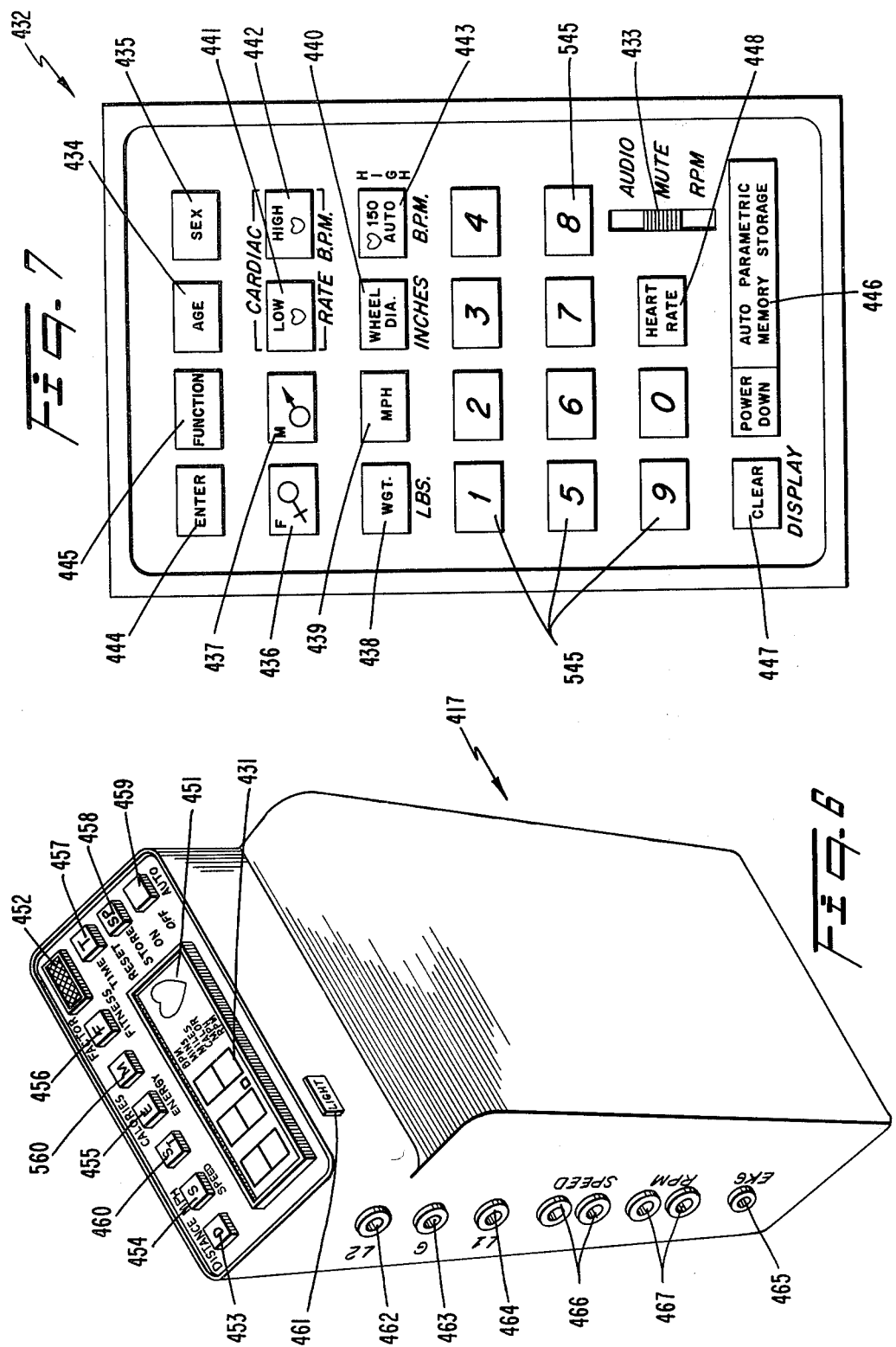

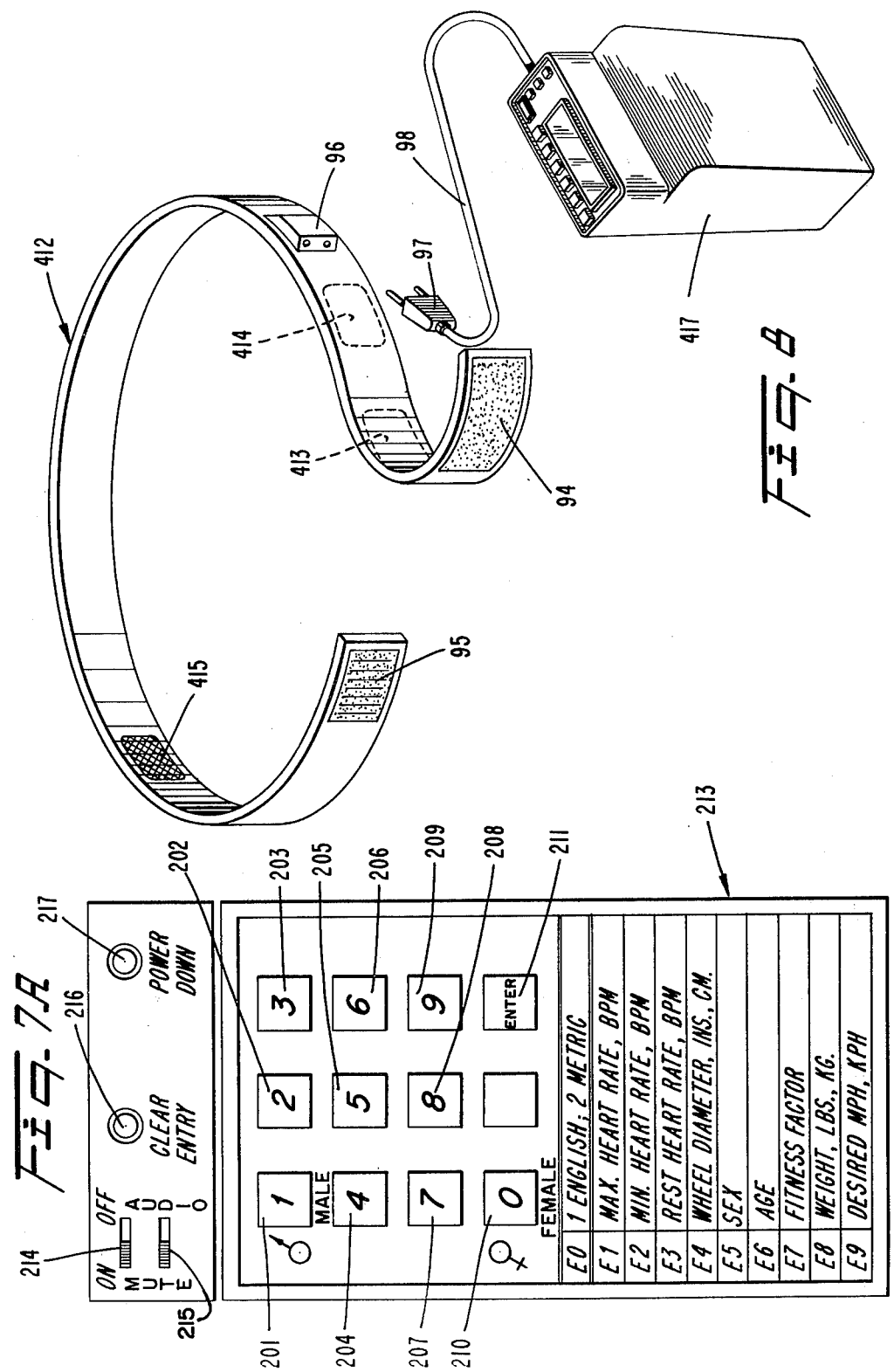

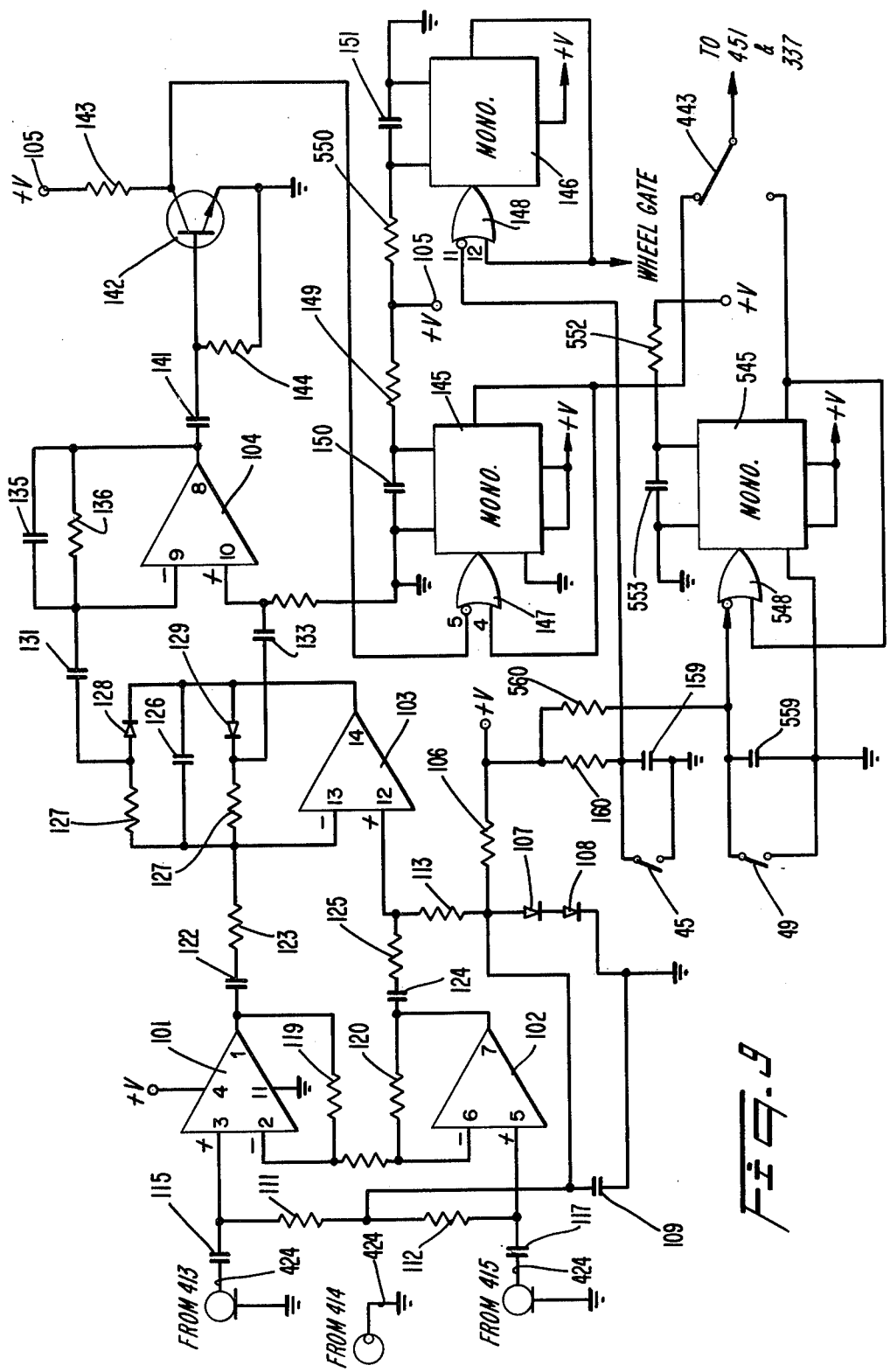

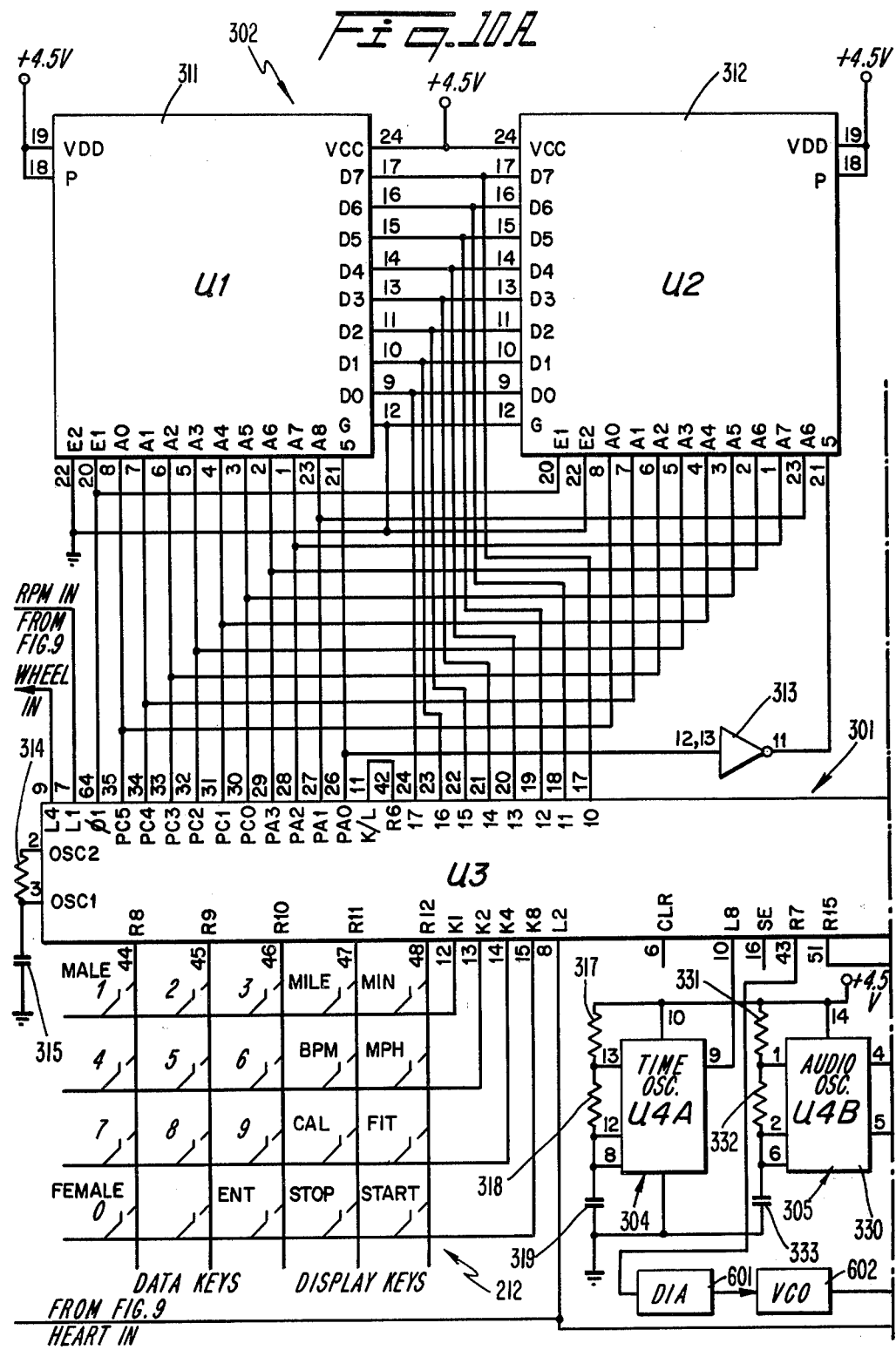

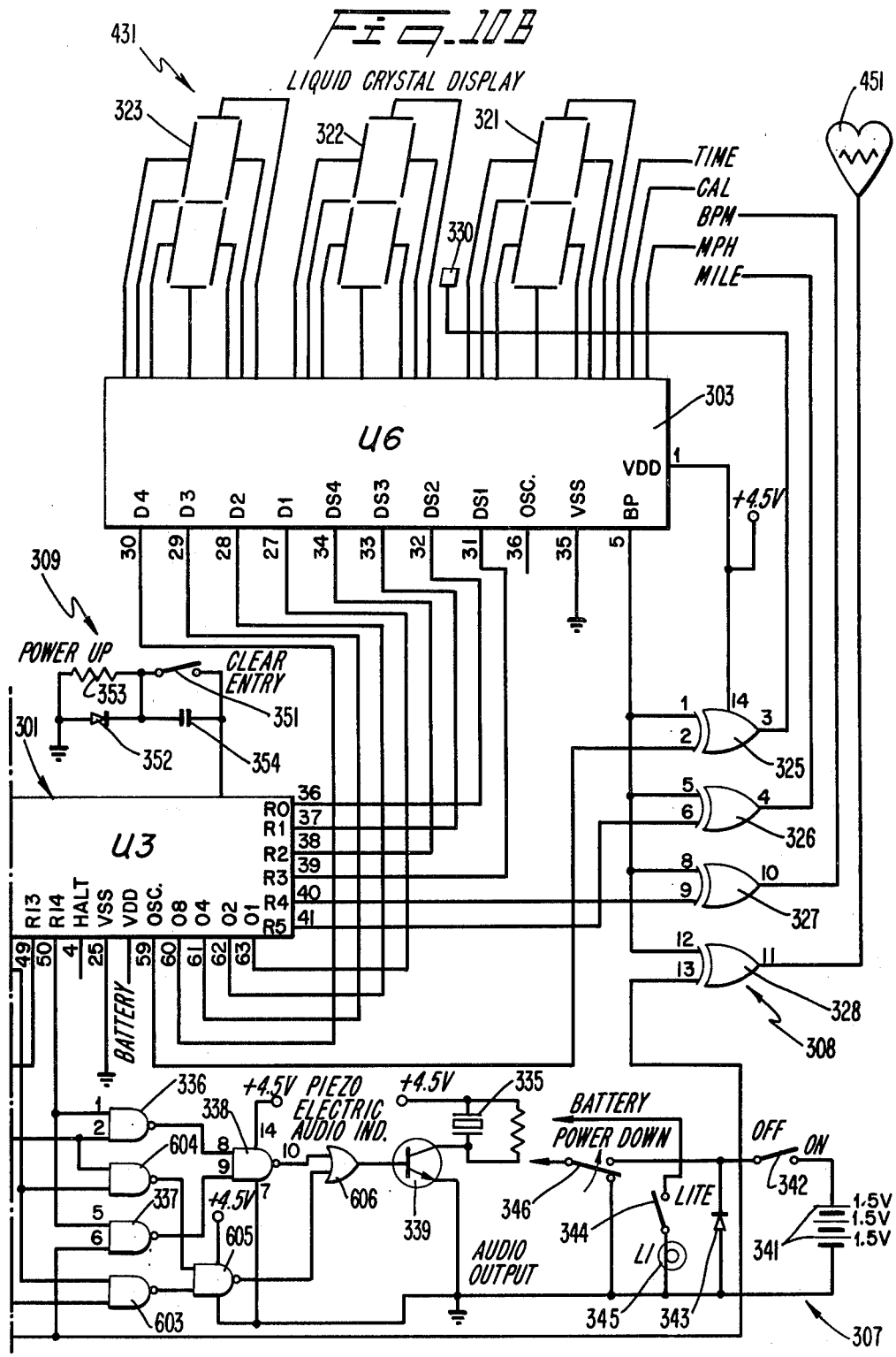

APPARATUS FOR TESTING PHYSICAL CONDITION OF A SELF-PROPELLED VEHICLE RIDER

RELATION TO CO-PENDING APPLICATION

The present invention is a continuation-in-part of our co-pending application entitled "Apparatus for Testing Physical Condition of a Subject", Ser. No. 145,765, filed Apr. 30, 1980 now U.S. Pat. No. 4,367,752.

TECHNICAL FIELD

The present invention relates generally to apparatus for testing the physical condition of a selfpropelled vehicle rider and more particularly to such an apparatus wherein the physical condition is determined in response to signals incicative of heart rate activity and distance traveled by the rider during testing.

BACKGROUND ART

In the co-pending application, there is disclosed an apparatus for testing the physical condition of a subject performing an aerobic exercise involving motion of a limb of the subject. Means are adapted to be mounted on the subject for monitoring and deriving a first signal indicative of heart activity of the subject. A second signal indicative of distance traversed by the subject during testing is derived. In the specifically disclosed embodiment of the prior application, the second signal is derived by a pedometer mounted in an instrument housing carried by the subject, who generally is a runner or jogger. At least one signal indicative of a predetermined, constant value physiologically relevant parameter of the subject, such as age, stride length, weight, is derived. A clock source derives a timing signal during testing of the subject. A computer responds to the different signals to derive a signal indicative of physical activity of the subject being tested. An indicator responds to the physical activity signal.

In the preferred embodiment, the housing includes a keyboard for enabling the signals indicative of the physiologically relevant parameters to be derived as numerical quantities. The housing also includes the clock source and the computer, as well as the indicator, both preferably of the digital type. Plural key switches on the housing are associated with the different physical activities to control activation of the indicator so that the indicator is selectively responsive to only one of the signals derived by the computer at a time.

BRIEF DESCRIPTION OF THE INVENTION

In accordance with one aspect of the present invention, the prior art device is modified so it is particularly adapted to determine the physical condition of a subject riding a self-propelled vehicle. The self-propelled vehicle is, in the preferred embodiment, a bicycle, which can be either of the moving or stationary type. The computer responds to the distance traversed by the subject while on the vehicle during testing, instead of a pedometer signal. The distance indicating signal is combined with the heart signal, physiologically relevant signals and timing signals in a computer which responds to these signals to derive an output signal indicative of the physical condition of the subject by utilizing formulae similar to those employed in the prior invention.

As a further feature, the present invention derives a signal indicative of the number of revolutions per unit time of the legs of a cyclist. Many cyclists, particularly those in competition, desire to maintain a relatively constant number of leg turns per unit of time. For example, the competitive bicycle racer desires to turn the pedals of his bicycle at a rate of between 90 and 120 revolutions per minute, while a typical touring cyclist should maintain a spinning rate of between 70 to 80 revolutions per minute. In accordance with one aspect of the present invention, a crank mounted permanent magnet couples magnetic flux into a reed switch mounted on a tube (either the seat tube or downtube) of a bicycle once each time pedals turn. Each time the permanent magnet passes the reed switch, the magnetic flux causes contacts of the reed switch to close, to supply a signal to the computer. The signal from the reed switch is combined in the computer with the timing signal to indicate pedal rotational velocity as revolutions per unit length of time, preferably revolutions per minute.

To provide an indication of the distance traversed by the bicycle rider, a spoke reflector, of the type required by the United States Department of Transportation on all bicycles sold in the United States, carries a permanent magnet interiorly thereof. The reflector carrying the permanent magnet is mounted on the spokes of the front or rear wheel of a bicycle to couple magnetic flux to a second reed switch mounted on a fork or one of the stays (such as a seat stay or chain stay) of the bicycle. Each time the permanent magnet carried by the reflector passes the second reed switch, the switch contacts of the second reed switch close to supply a pulse to the computer. The computer responds to pulses from the second reed switch and an input signal indicative of wheel diameter to derive a signal indicative of distance traveled. In addition, the signal from the second reed switch is combined with the timing signals to derive a signal indicative of vehicle speed, for example, in miles per hour.

A further feature of the invention is that housings for the reed switches are easily secured to and removed from the bicycle. To this end, housings for the reed switches are provided with hook and loop (Velcro) strips secured to Velcro strips carried on the bicycle. The permanent magnet can be magnetically secured directly to the pedal crank if the crank is made of suitable magnetic material; in the alternative, the crank mounted permanent magnet can be secured to the crank by a hook and loop strip.

In accordance with a further feature a pacing, i.e., cueing, signal for a cyclist is derived to assist the cyclist in riding a multi-gear, pedalled cycle at a desired speed. The vehicle speed and pedal rotational velocity signals are combined with a signal indicative of desired cycle speed to derive the pacing signal, preferably a beep that occurs once for each desired turn of the self propelled cycle, regardless of the gear in which the pedals are set.

It is, accordingly, an object of the present invention to provide a new and improved apparatus for testing the physical activity of a self-propelled vehicle rider.

A further object of the invention is to provide a new and improved apparatus for enabling the physical activity of a cyclist to be determined.

A further object of the invention is to provide a new and improved apparatus for enabling aerobic qualities of a cyclist to be determined.

Still another object of the invention is to provide a new and improved apparatus for enabling the speed of a self-propelled vehicle to be determined.

An additional object of the invention is to provide a new and improved device for enabling the speed of a cycle wheel having spokes to be determined.

Still a further object of the invention is to provide a new and improved device for enabling a velocity or distance indication of a rotary part of a cycle to be derived.

Yet another object of the invention is to provide a pacing signal to a cyclist of a multi-gear bicycle, to assist him in riding at a desired speed.

The above and still further objects, features and advantages of the present invention will become apparent upon consideration of the following detailed description of several specific embodiments thereof, especially when taken in conjunction with the accompanying drawings.

BRIEF DESCRIPTION OF THE DRAWING

FIG. 6 is a generally front, perspective view of an electronic instrument housing adapted to be carried by a cyclist, as illustrated in FIG. 1;

FIGS. 7 and 7a are back views of first and second embodiments of the instrument housing illustrated in FIG. 5;

FIG. 8 is a perspective view of an electrode carrying chest strap in combination with a cable and the instrument housing illustrated in FIGS. 6 and 7;

FIG. 9 is a circuit diagram of an electrocardiogram amplifier and circuitry responsive to closure of reed switches in the apparatus of FIGS. 2 and 4; and FIGS. 10a and 10b, together, constitute a block diagram of computer circuitry contained in the instrument housing, in combination with signal sources representing the reed switch closures and electrocardiogram signals.

BEST MODE FOR CARRYING OUT THE INVENTION

Figure 1:
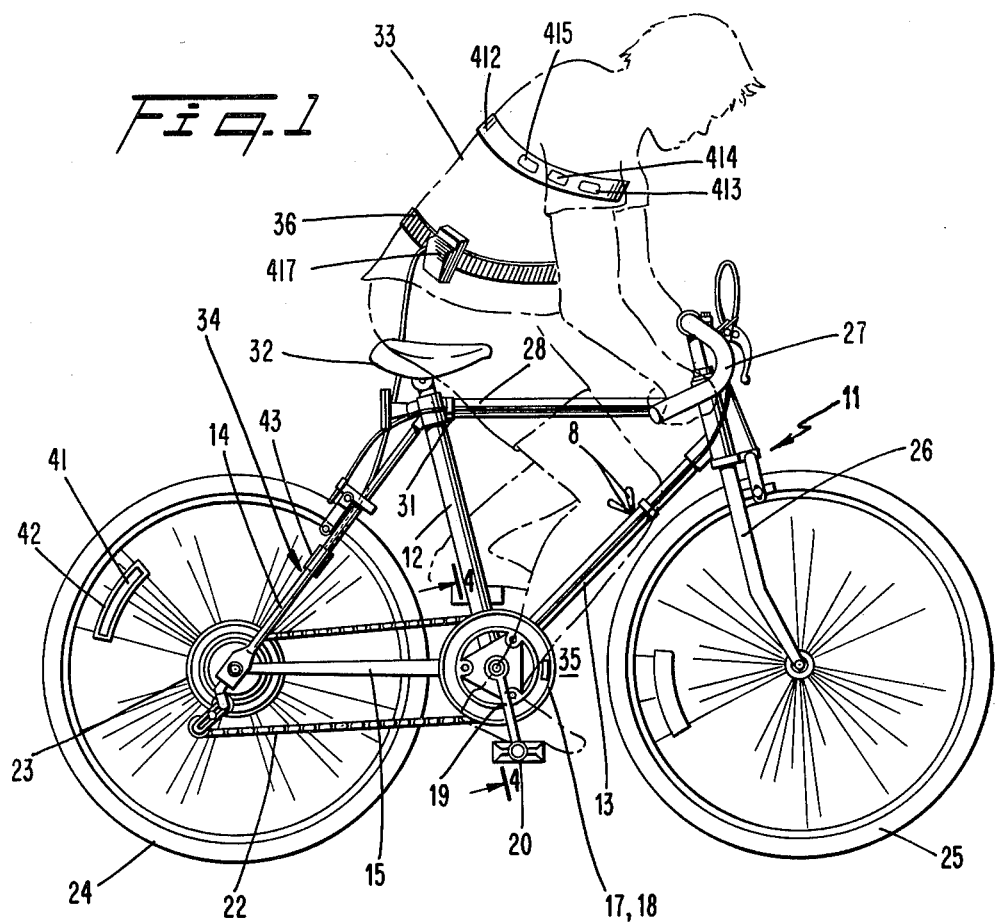
FIG. 1 is a diagram of a cyclist and cycle for enabling the physical activity of the cyclist to be determined, in accordance with a preferred embodiment of the present invention.

Reference is now made to FIG. 1 of the drawing wherein a self-propelled vehicle in the form of a multi-gear bicycle 11 is illustrated as including the usual seat tube 12, down tube 13 that carries gear levers 8, seat stays 14 and chain stays 15. At the intersection of tubes 12 and 13 with chain stays 15 is bottom bracket 16 in which is mounted sprocket assembly 9, including small and large diameter chain wheels 17 and 18, cranks 19 and pedals 20. Chain 22 extends between one of chain wheels 17 or 18 and multi-gear free wheel set 23 having a center coincident with an axle of rear spoked wheel 24, in turn coincident with the intersection of seat stays 14 and chain stays 15. Front, spoked wheel 25 is carried by fork blades 26, mounted on head tube 27. Extending in a generally horizontal direction from head tube 27 toward seat tube 12 is top tube 28, while a shaft of handle bars 29 extends vertically through head tube 27. Extending from seat tube 12, at the intersection of the seat tube 12, seat stays 14 and top tube 28 is seat post 31. Mounted at the top of seat tube 31 is saddle 32, on which male cyclist 33 sits during normal operation of bicycle 11.

The conventional, described bicycle 11 is modified in accordance with the present invention to include sensor assembly 34, enabling signals to be derived that enable the distance of bicycle 11 to be determined during a testing interval, as well as to enable the speed of the bicycle to be instantaneously determined. Bicycle 11 is also modified to include assembly 35, enabling signals to be derived that enable the rate of pedaling, in revolutions per minute, to be determined.

Cyclist 33 is equipped with a harness 412, including three electrocardiogram electrodes 413, 414 and 415 for transducing electric signals generated by the heart of cyclist 33 into electric signals. Appropriate leads extend between transducers 34 and 35, as well as between electrodes 413, 414 and 415 and instrument housing 417 carried by cyclist 33 on belt 36, that fits around the waist of the cyclist.

An electronic computer in instrument housing 417 responds to the signals in transducer assemblies 34 and 35, and an electrocardiogram signal from electrodes 413–415, as well as other input signals indicative of appropriate physiological characteristics of cyclist 33 and a characteristic of bicycle 11, to derive various signals indicative of physiological characteristics of the cyclist during a testing interval. In particular, transducer assembly 34 derives a pulse, which is applied by a suitable pair of leads to electronic circuitry in housing 417 each time rear wheel 24 makes a revolution. Each time sprocket assembly 9 makes a revolution, transducer assembly 35 supplies a pulse to the electronic circuitry in housing 417 via another suitable pair of leads. Each time cyclist 33 has a heartbeat, a characteristic pulse is supplied by electrodes 413–415 to the circuitry in housing 417 via a cable.

The electronic circuitry and computer in housing 417 respond to the signals from transducer assemblies 34 and 35, as well as from electrodes 413–415, and predetermined signals indicative of the age, sex and weight of cyclist 11, the diameter of wheels 24 and 25, and desired forward speed to generate various signals. The signals derived by the computer circuitry in housing 417 indicate distance traveled by cyclist 33 during the testing interval, the speed of the cyclist during the interval, the amount of calories expended by the cyclist during the interval, a fitness factor of the cyclist during the interval, the length of time during the interval, the instantaneous angular velocity, in revolutions per minute, of sprocket assembly 9, and a cue to assist the cyclist in maintaining a predetermined constant forward speed, regardless of the gear ratio between sprocket assembly 9 and rear wheel 24.

Figure 3:
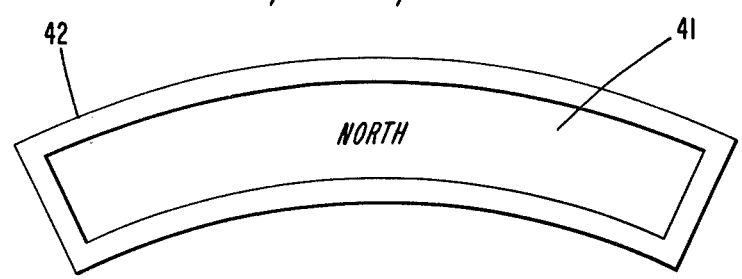
FIG. 3 is a front, sectional view of a reflector with a permanent magnet contained therein, in accordance with the present invention.

Rear wheel transducer 34 includes a bar-type permanent magnet 41 mounted in a conventional arcuately shaped reflector 42 that spans between a number of adjacent spokes on rear wheel 24. Reflector 42 is contained in plastic housing 40, mounted in a conventional way so that the inner and outer peripheries of the reflector are at predetermined radii of wheel 24, i.e., are at constant distances from the axle of the wheel. The reflective surface of reflector 42 is mounted on wheel 24 so it is substantially in the direction of wheel travel and can be seen by viewers broadside of the wheel. Similarly, bar magnet 41 is of arcuate shape so it fits easily into reflector 42 and enables the magnetic flux of the bar magnet to be at a substantially constant radius from the axle of wheel 24. To this end, opposite faces of bar magnet 41 are permanently magnetized with opposite polarities, indicated as N and S in FIG. 3, so magnetic flux lines cross the thickness of the magnet, whereby a single magnetic flux transition occurs across a region on one of seat stays 14 each time wheel 24 makes one complete revolution.

Figure 2:
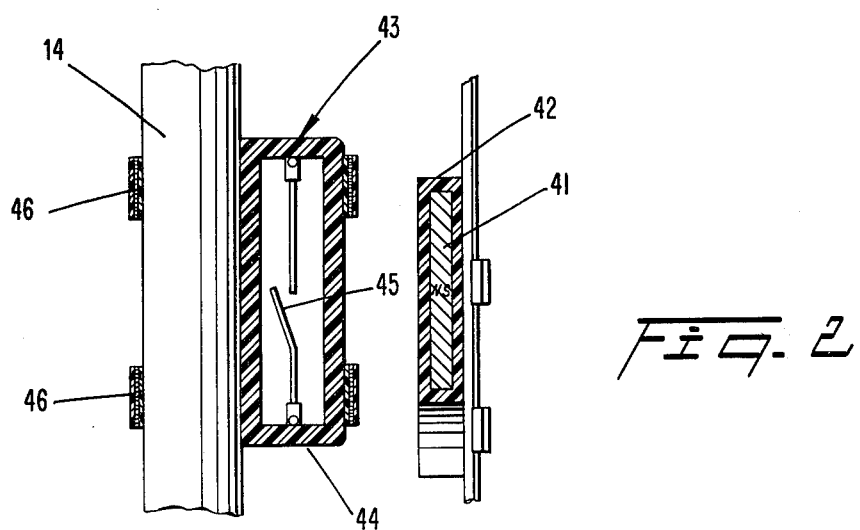
FIG. 2 is a diagram of a side, sectional view of an apparatus in accordance with the present invention for enabling the speed and distance travelled of a bicycle to be determined.

To sense the magnetic flux transition derived from magnet 41 once for each turn of rear wheel 24, reed switch assembly 43 is mounted on one of seat stays 14, at the same radial position as bar magnet 41. Reed switch assembly 43, as illustrated in FIG. 2, includes a plastic, nonmagnetic case 44 containing magnetically responsive contacts 45, positioned generally at right angles to the lines of flux from magnet 41. Leads extend along one of seat stays 14 from contacts 45 to couple indications of closure of the contacts to the instrument housing. Assembly 43 is selectively secured to one of stays 14 so that it is in close proximity to permanent magnet 41 when the permanent magnet passes the assembly. It is to be understood that magnet 41 can be mounted in front wheel reflector 542 in which case a reed switch assembly is mounted on fork 26 at the same radial position as reflector 542.

In operation, each time wheel 24 makes a revolution, magnetic flux is coupled from magnet 41 to reed switch contacts 45, causing the reed switch contacts to close. Each closure of reed switch contacts 45 causes a pulse to be derived in circuitry included in instrument housing 417. Circuitry is included in instrument housing 417 to prevent spurious signals from being derived, to assure that only a single pulse is derived by the circuitry for each revolution of rear wheel 24.

Figure 4:
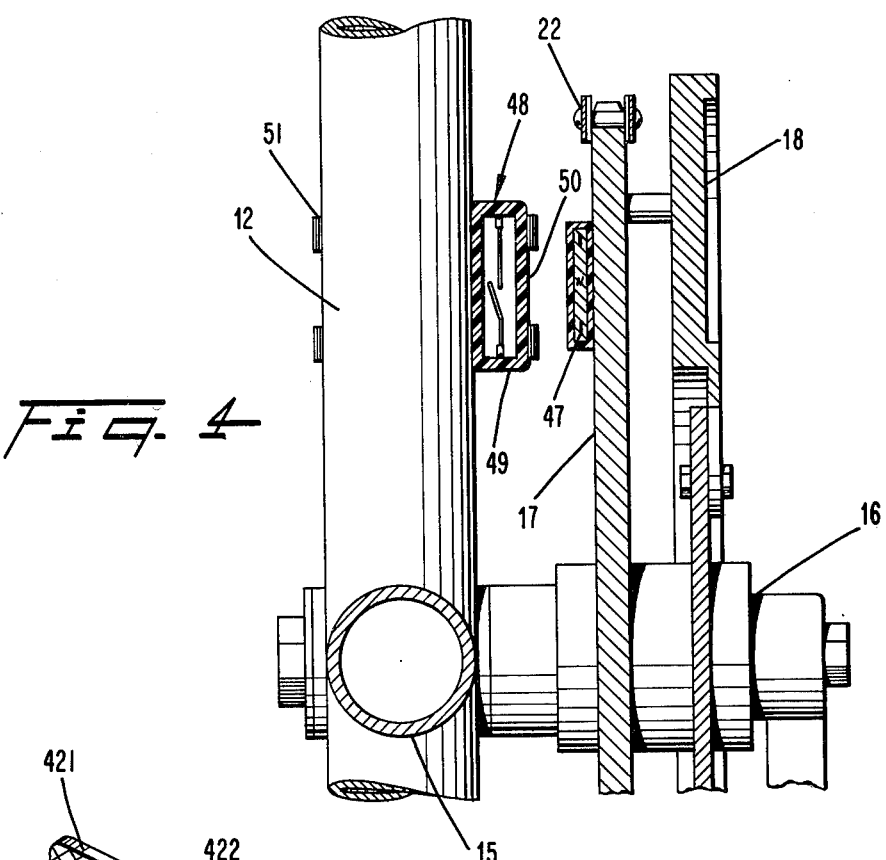
FIG. 4 is a side, sectional view of the permanent magnet reed switch combination for enabling the turning speed of pedals of a cycle to be determined.

As illustrated in FIG. 4, crank revolution per minute transducer 35 includes structure similar to that disclosed in connection with transducer 34. In particular, bar permanent magnet 47 is mounted on inner chain wheel 17, in proximity to reed switch 48, mounted on seat tube 12. Bar magnet 47 is positioned so that the opposed north and south pole faces (N and S) thereof extend radially of small chain wheel 17, on the face of the chain wheel in proximity to seat tube 12. If chain wheel 17 is fabricated of a magnetic material, permanent magnet 47 is secured to the chain wheel merely by the attractive magnetic force between the permanent magnet and the chain wheel. If, however, chain wheel 17 is manufactured of a nonmagnetic alloy, permanent magnet 47 is secured to the chain wheel by an appropriate adhesive, e.g., glue, double sided adhesive tape, or first and second Velcro strips, respectively secured to the chain wheel and to a radially extending arm of the chain wheel. Reed switch assembly 48 includes reed switch contacts 49, enclosed by a nonmagnetic, plastic housing 50 selectively secured to a side of seat tube 12 in proximity to the face of chain wheel 17 that carries permanent magnet 47. Housing 50 and permanent magnet 47 are spaced from bottom bracket 16 by the same distance so that they are radially aligned once during each turn of chain wheel 17.

In operation, once during each revolution of chain wheel 17 magnetic flux is coupled from permanent magnet 47 to contacts 49, causing the contacts to close. Closure of contacts 49 causes an electric signal to be coupled by leads which extend along seat tube 12 to instrument housing 417. Circuitry within instrument housing 417 responds to pulses derived in response to closure of contacts 49, to assure that only one pulse is derived in response to each revolution of free wheel 17.

Reed switch housings 43 and 48 are respectively held in situ on stay 14 and seat tube 12 by securing layers 501, 502, 503 and 504 of double backed adhesive tape to each of reed switch housings 43 and 48, seat tube 12 and stay 14. Attached to tape layers 501-504 on tube 12, stay 14 and reed switch housings 43 and 48 are respectively Velcro strips 505-508, to enable the reed switch housings to be easily removed from the seat tube and stay. Permanent magnet 47 can be similarly secured to the inner face of small chain wheel 17. Thereby, housings 43 and 48 are respectively rigidly held in situ on one of stays 14 and seat tube 12, but can be easily removed when cyclist 33 does not desire to test himself or if it is decided to utilize the housings on another bicycle.

Referring again to FIG. 1, electrodes 412, 413 and 414 are mounted on male cyclist 33. Electrodes 412, 413 and 414 are electrically connected to skin of cyclist 33 to derive electrocardiogram voltages generated by the subject. Electrodes 413, 414 and 415 are carried on a garment, in the form of chest strap 12, worn slightly above the vicinity of the male breast. If the cyclist is a female, electrodes 413, 414 and 415 are carried by a garment in the form of a brassiere, preferably of the type known as a "running bra" to minimize breast bouncing, skin irritation and collagen tissue breakdown of the breasts. Chest strap 412 is provided with a fastener (not shown) for firmly securing the chest strap to the chest of the subject so that electrode 413 abuts on the skin of the subject just below the right chest quadrant, electrode 414 abuts on skin against the sternum of the subject, in the center of the chest, and electrode 415 abuts on skin against the rib cage, in the vicinity of the heart. For a female subject, the brassiere forces the electrodes against the skin in the same body locations.

Figure 5:
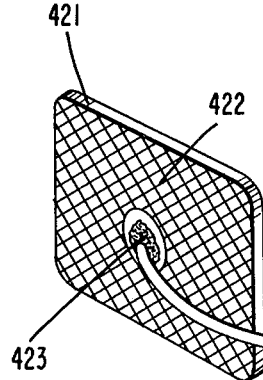
FIG. 5 is a generally perspective view of an electrode employed with the present invention.

A preferred configuration for each of electrodes 413-415, illustrated in FIG. 5, includes a generally square layer 421 of a highly electrically conductive gel which adheres to the skin of the subject while moistened. Layer 421 is illustrated as being of generally square configuration, but it is to be understood that it can take any suitable geometry having sufficient contact area on a face adapted to contact the skin of the subject. On the face of layer 421 opposite from the face adapted to contact the skin of the subject is a metal mesh layer 422 of stainless steel or soft annealed brass carrying an impregnated silver-silver chloride film. Layer 422 includes a central button 423, secured to lead wire 424 of a shielded or unshielded cable connected to a reference potential (preferably zero or ground voltage) within instrument housing 417. Lead wires 424 for each of electrodes 413-415 has a separate shield in one embodiment; in another embodiment the lead wires for the various electrodes have a common shield in a single cable. However, the latter configuration may have deleterious results due to cross coupling of signals transduced by electrodes 413-415.

In a preferred configuration, gel layer 421 is composed of the following ingredients: karaya gum, a hydrophilic carbohydrate polymer gum, exuded from certain Indian trees of the genus Sterculia, 33% by weight; glycerin, 60% by weight; ethanol, 1% by weight; methyl-p-hydrooxybenzoate, 0.01% by weight; propylp-hydroxybenzoate, 0.01% by weight; sodium chloride, 4% by weight; potassium chloride, 2% by weight. The karaya gum forms a highly electrically conductive translucent colloidal gel when mixed with the remaining ingredients. Layer 421 has an area of approximately 4 cm×4 cm and a 2 mm thickness. If desired or necessary, layers 421 are moistened with water or a saline solution prior to the subject securing chest strap 412 or a brassiere in place. Alternatively, layer 421 remains dry prior to installation and is moistened by perspiration from the skin of the cyclist.

It is to be understood that other electrodes can be utilized in lieu of the electrodes specifically illustrated in FIG. 5. In particular, In-Vivo Metric Systems type E221 electrode or a Beckman Instruments company type 650437 electrode could be employed. If either of these electrodes is used, however, an electrolyte gel must be employed to provide proper coupling of the electrocardiogram voltage to lead 24. It is also to be understood that other gum type electrodes can be employed.

Reference is now made to FIGS. 6 and 7 wherein there is illustrated the exterior of electronic instrument housing 417, carried on waistband 416. Inside of housing 417 is located electronic circuitry responsive to signals derived from electrodes 413–415, as well as from transducer assemblies 34 and 35. Housing 417 also includes a clock source for deriving a timing signal and digital computer means responsive to the electrode signals. The computer responds to the signals from transducer assemblies 34 and 35, predetermined physiological parameters concerning cyclist 32 and a signal indicative of the diameter of wheels 24 and 25. The computer means derives a signal indicative of the physical activity of cyclist 33 and supplies the signal to an indicator, in the form of a liquid crystal digital display 431 mounted on the top face of housing 417. Housing 417 is shaped generally as a right parallelpiped, having approximately a 6 inch length, 3 inch width and a 1 inch thickness.

Physiologically relevant data concerning cyclist 33 being tested are entered into the computer means with keyboard 432 on the back face of housing 417, i.e., the housing face adjacent the body of cyclist 33. Keyboard 432 includes a matrix of keys for enabling the wheel diameter, differing, predetermined, constant physiologically relevant parameters and differing numbers related to some of these parameters to be entered into the computer. Other keys and slide switch 433 are respectively provided for functions associated with clearing entries, data storage in a memory of the computer means and the types of indications (aural and/or visual) provided by housing 17. The predetermined, constant physiologically relevant functions which can be entered are age, sex (male or female), and weight of the cyclist 33; these entries are respectively associated with keys 434, 435, 436, and 437. In addition, keys 441 and 442 are respectively associated with resting heart rate, (low) and maximum heart rate (high), for cyclist 33; the maximum heart rate is determined from a chart supplied to the cyclist or to a physician who is testing the cyclist. Key 443 is for selective entry of a maximum heart beat rate of 150 beats per minute, for those subjects who have been clinically found to have a maximum heart rate of 150 beats per minute; a significant (25%) portion of the population has a congenital heart defect such that they should not have a heart rate greater than 150 beats per minute. Key board 432 also includes keys 439 and 440, respectively associated with desired forward speed (in miles per hour) and diameter of wheels 24 and 25 (in inches; if wheel diameter is the entered parameter, it is multiplied by 3.142 in the computer to derive an indication of circumference). Key 439 is used in conjunction with slide switch 433. If key 439 is not activated and switch 433 is set at the "audio" position an aural pulsed tone is derived for each heart beat of the cyclist, while a continuous aural tone is derived if the heart beat rate exceeds a predetermined, emergency value. If key 439 is activated and switch 433 is set at the "audio" position, an aural pulsed tone is generated to enable a pulsed tone to be derived once for each each revolution of cranks 19 for a desired turning rate of the pedals to achieve a desired speed of the bicycle. If key 439 is activated the aural pulses are derived at a variable frequency determined by the entry following the key activation and the bicycle gear ratio, as calculated by the computer in response to the signals from transducers 34 and 35.

In general, an entry is made by depressing function key 445, then pressing physiological key or keys associated with the particular physiological factor, then numeral keys 545 or a specific sex key 436 or 437, in turn followed by depressing enter key 444. For example, if a male subject is known to have the congenital heart defect, function key 445 is pressed, then key 443 is pressed, in turn followed by pressing of enter key 444. Then after function key 445 is again depressed sex key 435 is depressed, followed by pressing male key 436, in turn followed by depression of enter key 444. After a further depression of function key 445 one of keys 434 or 438–442 is pressed, followed by entry of a numerical value by pressing one or more of 0-9 numeral keys 545, followed by depressing enter key 444. These operations are repeated for each of keys 434 and 438–442.

Keyboard 432 includes three additional keys 446, 447 and 448, respectively labeled "power down", "clear" and "heart rate". Depressing of "power down" key 446 enables the physiological parameters associated with cyclist 33 to be stored in a memory of the computer within housing 447 indefinitely, even when power is decoupled from the remainder of the unit. If the physiological parameters of the subject change or the device is used for a different subject, new parameters can be entered into the memory merely by pressing function key 445, the desired physiological key, the specific sex or numerical value keys or enter key 444. Clear key 447 is depressed when it is desired to remove all entries from keyboard 432 and to clear display 431. Heart rate key 448 is depressed by the subject while he is in a rest condition and after chest strap 412 is secured in place so leads 424 of electrodes 413–415 are connected to input terminals of instrument housing 417.

On the top face of instrument housing 417, in addition to liquid crystal display 431, are a liquid crystal display 451, in the form of a heart, and a cloth or other air pervious screen 452, for allowing aural pulses and continuous aural tones to be coupled exteriorly of housing 417 to be heard by cyclist 33. Liquid crystal display 451 is activated simultaneously with the derivation of heart beats of the subject. Alternatively, liquid crystal display 451 can be activated in response to pulses derived from transducer 35 each time sprocket assembly 9 makes a complete revolution. With slide switch 433, on the back face of instrument housing 417 in an upper "audio" position, an aural pulsed tone is coupled through screen 452 each time the heart of the subject beats, when the heart beat rate is greater than the rate which is entered after depression of low rate key 441. A continuous aural tone is coupled through screen 452 in response to the heart beat rate of the subject exceeding a predetermined maximum, associated with entry of a numerical key value subsequent to depression of high rate key 442 or 150 rate key 443. If slide switch 433 is in the "audio" upper position, the subject is advised to reduce his activity if the continuous tone is heard. With switch 433 in the upper position and if key 439 was activated a pulsed aural cueing tone is coupled through the screen once each time the cyclist should complete a pedal revolution to maintain a predetermined speed. With slide switch 433 in a center "mute" position, no aural tone is coupled through screen 52. With slide switch 433 in the lower "rpm" position, a pulsed aural tone is coupled through screen 452 once for each revolution of pedals 19.

On the upper face of housing 417 are nine additional keys 453–460 and 560, respectively associated with the output functions: distance traversed (D key 453), average speed (S key 454), calories or energy consumed (K key 455), fitness factor (F key 456), elapsed time of exercise (M key 457), stop time of exercise/store (SP key 458), beats per minute (key 459), start time of exercise (ST key 460), and revolutions per minute (RPM key 560).

After an exercise routine has been completed, e.g., by riding bicycle 11 for 12 minutes, during which signals were supplied to the computer by transducers 34 and 35, electrodes 413–415, and the clock source, the numerical values of the various parameters associated with keys 453–457 and 560 are read from display 431 in response to depression of stop time of exercise/store key 458, followed by depression of keys 453–457 and 560. Display 431 is supplied by the digital computer in instrument housing 417 with a distance traveled signal derived directly by multiplying the number of pulses derived from transducer 34 by the wheel diameter input from keyboard 432 and an appropriate factor in response to depression of keys 458 and 453. In response to depression of keys 458 and 454, the computer in instrument housing 417 responds to signals in the memory thereof indicative of the calculated distance and elapsed time to supply display 431 with a signal indicative of average speed of bicycle 11 during testing. In response to depression of keys 458 and 455, the computer responds to the signals from electrodes 413–415 and the elapsed time and distance signals stored in the memory thereof to supply display 431 with an indication of the number of calories consumed by the cyclist during the testing period. In response to depression of keys 458 and 456, the computer again responds to the signals from electrodes 413–415 and the stored calculated values of distance and elapsed time to provide an indication of maximum oxygen uptake, a function correlated with a fitness factor for cyclist 33. In response to depression of keys 458 and 560, the computer responds to the signals from transducer 35 and the determined elapsed time to provide an indication of average revolutions per minute during the testing interval.

At the beginning of the exercise routine, stop/store key 458 is depressed and then start key 460 is depressed to initiate operation of a timing or clock signal within the computer. During the exercise routine, any of the parameters, except the fitness factor, can be determined by depressing one of keys 453–455, 457 or 560; for example, the elapsed time of the exercise period is determined by depressing M key 457. After the exercise routine has been completed, stop/store key 458 is depressed once to decouple the signals from transducers 34 and 35 and from electrodes 413–415, and to decouple the timing signals from the computer in instrument housing 417.

Thereafter, any of keys 453–457 and 560 can be depressed to enable the desired information to be read from display 431. After the exercise routine has been completed and all of the desired variables have been read from display 431, power down key 446 is depressed, causing the calculated and input parameters to remain in memory indefinitely while decoupling power from the aural signal source and displays 431 and 451. If data storage is not desired, on/off key 459 is depressed to remove power from the memory and inactivate displays 431 and 451, as well as to prevent derivation of aural signals.

If a liquid crystal display is provided, display 431 is energized immediately in response to depression of keys 453–457 and 560. If the device is used at night, the liquid crystal displays 431 and 451 are illuminated by light emitting diode 461, on the front face of housing 417, immediately below display 431, in response to depression of any of keys 453–457 and 460.

On one of the side walls of instrument housing 417 are located jacks 462, 463 and 464 for the shielded cables surrounding leads 424 connected to electrodes 413–415. Alternatively, jacks 462–464 can be replaced by a single female connector adapted to receive prongs of a male connector in a single cable connecting electrodes 413–415 to electronic circuitry within instrument housing 417. At the bottom of this side wall is a further jack 465 for enabling an EKG signal picked up by electrodes 413–415 to be supplied to a conventional electrocardiogram paper tape recorder; the latter feature is utilized only when the device is testing a cyclist on a stationary bicycle where it is convenient to connect an EKG paper tape recorder to jack 465.

On the same side wall on which are located jacks 462–465 are located jack pairs 466 and 467, adapted to be connected to leads connected to the reed switches of transducers 34 and 35, respectively. To prevent incorrect connection of the leads from transducers 34 and 35 into jack pairs 466 and 467, jack pair 466 has a diameter greater than the diameter of the jacks in pair 467.

Reference is now made to FIG. 7a of the drawing wherein there is illustrated a second embodiment of instrument housing 417. In the embodiment of FIG. 7a, the number of keys is reduced compared to the number of keys in the embodiment of FIG. 7. Key activation is associated with and directed in response to command indicia supplied to display 431. In response to the indicia of display 431 having certain values, the operator of the keyboard illustrated in FIG. 7a makes certain entries, as directed by printed table 213, positioned below keys 201–211 on keyboard 212. Keyboard 212 includes ten numeral keys 201–209 and 210, respectively provided for the numerals 1–9 and 0. Keys 201 and 210, in addition to being associated with the numerals 1 and 0, are function keys for entry of male and female genders of the cyclist. A further key 211, for enabling entry of numbers and functions associated with the remaining keys, is also provided.

In the embodiment of FIG. 7a, immediately above keyboard 212, are additional keys 214–217 associated with various functions. In particular, there is an on-off toggle switch 214, as well as a three-position toggle switch 215, which enables activation and deactivation of the aural signal derived from the speaker behind screen 452 in response to each heartbeat of the cyclist, the heartbeat exceeding a predetermined rate and the desired forward speed cue or in response to each complete revolution of sprocket assembly 9. To the right of switches 214 and 215 are keys 216 and 217, respectively provided for clearing entries into keyboard 212 and the power down operation for enabling the memory in the computer to store information indefinitely without power being supplied to visual indicators 431 and 451, as well as to the aural signal source.

In use, toggle switch 214 is slid to the on position, after electrode strap or harness 412 has been secured in place, but before electrodes 413-415 have been connected to terminals 462-464. In response to toggle switch 214 being activated to the on condition, the programmed computer in housing 417 activates display 431 to cause characters E0 to be displayed on display 431. Printed table 213 below keyboard 212 provides the operator with an indication that E0 involves selecting English or metric measurement units. The operator activates key 201 for selection of English units; key 202 is activated for metric selection. After key 201 or 202 has been pressed the computer activates display 431 to cause characters E1 to be displayed. Table 213 advises the operator that E1 is maximum heart rate, in beats per minute. The operator then activates keys 201-210 with maximum heart rate for the subject, as determined from a table. After entry of the maximum heart rate, display 431 is activated to indicate the numerical values associated with depressed keys 201-210. The operator then looks at display 431 to assure that the correct keys have been depressed. If he is satisfied that the correct keys have been depressed, enter key 211 is depressed. After depression of entry key 211, display 431 is activated by signals from the computer within housing 417, to display characters E2. The operator is then advised from printed table 213 that he is to enter minimum heart rate, in beats per minute, as determined from a table. The process is then repeated for resting heart rate, in beats per minute determined upon awakening, and wheel diameter or circumference, in inches or centimeters, in accordance with entries E3 and E4, respectively, from printed table 213.

After wheel diameter or circumference has been entered by activating key 211, display 431 is energized by the computer in housing 417 to display characters E5. In response to display of E5 on display 431, the operator presses key 201 or 210, depending upon whether the cyclist is a male or female. Then, the computer supplies display 431 with a signal causing characters E6 to be displayed. Thereafter, the operator enters the age, fitness factor and weight in pounds or kilograms, for the cyclist in response to the computer energizing display 431 for the characters E6, E7 and E8. Fitness factor can be determined from a table or a previous calculation by the computer. After the weight entry, characters E9 are displayed to advise the operator to enter desired bicycle speed, in miles per hour or kilometers per hour. If the operator wants to be supplied with the once per revolution aural cue signal for the desired speed, he enters the desired speed by depressing keys 201-210 appropriately. If the operator does not desire the speed aural cue signal the numeral 999 is entered by pressing key 209 three times.

If the operator realizes that he has made an entry error after enter key 211 is depressed, clear entry button 216 is depressed. In response to depression of key 216, the program in the computer within housing 417 goes back to a starting condition, wherein characters E1 are again indicated on display 431. The operator then goes through the sequence E0-E9.

After all of the parameters associated with the sequence E0-E9 for the cyclist have been entered, electrodes 413-415 in harness 412 are connected to the computer by way of jacks 462-464. Then, leads connected to reed switches 43 and 48 of transducers 34 and 35 are connected to jack pairs 466 and 467. The operator then presses start key 460 on the top of housing 417, after which heart rate key 459 is depressed. The operator then monitors display 431 to observe the heart rate of the subject, to verify that electrodes 413-415 are correctly connected. Then, the operator presses start key 460, after which speed key 454 is depressed, while rear wheel 24 is lifted from the ground and pedals 19 are turned. The operator then monitors display 431 to observe the number indicated by display 431, to verify that the leads of transducer 34 are correctly connected. Then, the operator presses start key 60, after which RPM key 560 is depressed, while rear wheel 24 is lifted from the ground and pedals 19 are turning. The operator then monitors display 431 to observe the number indicated by display 431, to verify that reed switch 48 of transducer 35 is correctly connected.

Housing 417 is then attached to waistband 416 or harness 412. When the cyclist is ready to begin cycling, stop/store key 458 is depressed, followed by depression of start key 460. While the cyclist is cycling, the parameters of interest can be monitored by pressing any one of keys 453, 454, 455, 457, 459 or 560. With three-position switch 215 in the left position, as illustrated, the aural indicator is activated each time a heart beat occurs, if the heart beat rate reaches a minimum value set in response to characters E2 unless a number other than 999 is entered after display of E9. If the maximum heart rate set in response to characters E1 is exceeded, the aural signal is constantly derived. If a number other than 999 is entered after display of E9, the aural indicator is activated at a variable rate commensurate with each pedal turn necessary to achieve a desired forward speed regardless of the bicycle gear ratio. If fitness coefficient is desired, the exercise routine is performed for 12 minutes, after which time key 456 is depressed. With switch 215 in the right position, the aural indicator generates a pulsed aural signal each time a revolution of pedals 19 is completed.

An arrangement for connecting electrodes 413-415 of chest strap 412 to instrument housing 417 is illustrated in FIG. 8. Chest strap 412 is fabricated of a flexible cloth material having hook and loop fastener pads 94 and 95 at opposite ends thereof. Electrodes 413-415 are sewn into chest strap 412 so that gel layers 421 thereof are exposed on the interior surface of the strap. Lead wires 424 from electrodes 413-415 extend interiorly through chest strap 412 to male connector 96, mounted on the outside of the chest strap. Connector 96 includes three female pins, surrounded by a metal shield. The three female pins and shield of connector 96 are selectively engaged by male connector 97, at one end of cable 98, having another end including a male plug received by female connector on a side of housing 417.

The voltages picked up or transduced by electrodes 413-415 have a tendency to drift in common relative to a reference, i.e., ground, potential of the circuitry included within instrument housing 417. Circuitry is provided in instrument housing 417 to eliminate this drift, i.e., to provide common mode rejection. In addition, the circuitry filters out noise in electrocardiogram signals transduced by electrodes 413-415 and detects R pulses in the PQRST complex of pulses derived each time a heart beat of the cyclist occurs. Processing circuitry in housing 417 responds to signals transduced by electrodes 413-415 to eliminate noise on the signal manifested by the occurrence of high amplitude pulses having a frequency greater than the possible heart beat rate of the cyclist.

To these ends, the processing circuitry in housing 417 for the voltages transduced by electrodes 413-415 and for initially processing pulses from contacts 45 and 49 of transducers 34 and 35 is preferable as illustrated in FIG. 9. The circuitry illustrated in FIG. 9 is hybrid circuitry, including four differential, operational amplifiers 101-104 mounted on a common integrated circuit chip and having a common positive DC power supply terminal. Amplifiers 101-104 respond to the EKG signal transduced by electrodes 413-415 and are connected to discrete components enabling a pulse to be derived each time an R pulse occurs in a QPRS complex of the subject. Lead wire 424 of electrode 414 is connected to ground potential within instrument housing 417 as are the common or individual shields associated with lead wires 424 of electrodes 413-415.

For common mode rejection, the voltages on lead wires 424 from electrodes 413 and 415 are differentially combined in amplifiers 101, 102 and 103. The voltages on lead wires 424 from electrodes 413 and 415 are supplied to non-inverting input terminals of operational amplifiers 101 and 102; these non-inverting terminals are also connected to a positive DC power supply voltage at terminal 105. The supply voltage at terminal 105 is derived from a battery, typically a 4.5 volt source, inserted through a suitable opening (not shown) in housing 417. The voltage at terminal 105 is reduced and regulated by a circuit including resistor 106, shunted by capacitor 109 and series diodes 107 and 108. The DC voltage developed across capacitor 109 is coupled to non-inverting input terminals of amplifiers 101-104, enabling these amplifiers to respond to both positive and negative DC voltages even though a single, positive DC power supply is provided. Non-inverting input terminals of all of amplifiers 101-104 are referenced to a common potential across capacitor 109, by virtue of the connection of resistors 111-113 to non-inverting input terminals of the amplifiers and a common terminal for resistor 106 and capacitor 109.

Amplifiers 101 and 102 are respectively coupled to voltages derived from electrodes 413 and 415 by first and second series circuits respectively including capacitors 115 and 117. The gains of amplifiers 101 and 102 are stabilized by feedback resistors 119 and 120, respectively connected between the output terminals of amplifiers 101 and 102 and inverting input terminals of these amplifiers. The output voltages of amplifiers 101 and 102 are respectively AC coupled to negative and positive input terminals of amplifier 103. The output signal of amplifier 101 is coupled to the inverting input terminal of amplifier 103 by a series circuit including capacitor 122 and resistor 123, while the output signal of amplifier 102 is coupled to the non-inverting input terminal of amplifier 103 by a series circuit including capacitor 124 and resistor 125.

To provide a low pass filter effect and full wave rectification for the voltages supplied to the inverting and non-inverting input terminals of amplifier 103, a feedback circuit is provided between the amplifier input and output terminals. The feedback circuit includes three parallel branches, each connected between the output and inverting input terminals of the amplifier. In one of the branches is connected smoothing capacitor 126, while each of other two branches includes a separate current limiting resistor 127; each of resistors 127 is connected in series with oppositely polarized diodes 128 and 129.

Negative and positive voltages are respectively developed at the anodes and cathodes of diodes 128 and 129. The negative and positive voltages are respectively coupled to inverting and non-inverting input terminals of amplifier 104 by way of two separate high pass series resistance-capacitance circuits. In particular, the anode of diode 128 is connected to the inverting input terminal of amplifier 104 by series capacitor 131 while the voltage at the cathode of diode 129 is coupled to the non-inverting input terminal of amplifier 104 by series capacitor 133. A feedback circuit including the parallel combination of capacitor 135 and resistor 136, between the output and inverting input terminals of amplifier 104, provides low pass filtering for the differential signal derived at the output of amplifier 104.

Because of the full wave rectifying effect of diodes 128 and 129 and the differential connections between the outputs of amplifiers 101 and 102 to the input terminals of amplifier 103 and the dual outputs of amplifier 103 at diodes 128 and 129, the output of amplifier 104 is always a positive voltage, regardless of the manner in which the leads from electrodes 413-415 are connected to the circuitry within instrument housing 417. The circuitry described is a precision full wave, rectifying amplifier so the output voltage of amplifier 104 is a positive voltage that is a relatively accurate replica of each R pulse in a PQRST complex, regardless of whether electrode 413 or 415 is coupled to the inverting input terminal of amplifier 101, and regardless of whether the voltage from electrode 415 and 413 is coupled to inverting input terminal of amplifier 102.

Resistors 111, 112, 123 and 125, as well as capacitors 115, 117, 122, 124, 131 and 134, form a high pass filter having a cutoff frequency of approximately 16 Hertz and a roll-off of 18 db per octave. Capacitor 126, resistor 127, capacitor 135 and resistor 136 form a low pass filter having a cut-off frequency of approximately 34 Hertz, with a roll-off of 12 db per octave. The resulting band pass filter derives a wave that is an accurate replica of the R wave of the PQRST complex with common mode rejection, to enable the R pulse to be stabilized to a DC reference and minimize noise which might be picked up by electrodes 413-415.

The R pulse in a PQRST complex, being the highest amplitude pulse in the complex, is supplied to a clamping circuit including series capacitor 141 and normally backed biased NPN transistor 142, having a collector electrode connected to the DC power supply voltage terminal 105 by resistor 143. The emitter collector path of transistor 142 is normally back biased to cut off by resistor 144, directly shunting the transistor emitter base junction which functions as a shunt diode. In response to the R pulse being derived from the output of amplifier 104, the emitter base junction of transistor 142 is forward biased, whereby current momentarily flows through collector resistor 143, to lower the voltage at the collector of transistor 142 virtually to ground, and the base-emitter junction of transistor 142 functions as a diode. The diode action of the emitter base junction of transistor 142 causes the base circuit of the transistor to function as a positive peak detector for the R pulse, whereby the base of transistor 142 can rise only about 600 millivolts above ground, but it can be driven considerably below ground in response to the output of amplifier 104. The negative voltage at the base of transistor 142 decays relatively slowly toward ground because of a 100 millisecond time constant of capacitor 141 and resistor 144, thereby virtually assuring a one-to-one relation between heart beats of the subject and the negative going pulses derived at the collector of transistor 142.

It is possible that noise may forward the base emitter path of transistor 142. Such noise is likely to occur at a frequency higher than the possible maximum heart beat rate of a cyclist; typically the maximum heart rate is approximately 240 beats per minute, i.e., 4 beats per second. To prevent such noise from being erroneously indicated as a heart beat, a timing circuit including one shot multivibrator 145 is provided.

One shot multivibrator 145 is part of a one shot integrated circuit chip also including one shot multivibrators 146 and 545, respectively responsive to closures of reed switch contacts 45 and 49 of distance monitoring transducer 34 and pedal RPM monitoring transducer 35. One shots 146 and 545 are connected to be responsive to switch contacts 45 and 49 so that a pulse is derived from each of circuits 146 and 545 each time wheels 24 and pedals 19 respectively make one revolution. One shots 146 and 545 include circuitry to enable the one shots to derive a single pulse for each revolution of rear wheel 24 and each revolution of pedals 19, even if there is a tendency for reed switch contacts 45 and 49 to bounce.

One shots 145, 146 and 545 include trigger input terminals respectively responsive to the outputs of OR gates 147, 148 and 548. OR gate 147 includes an inverting input terminal responsive to the voltage at the collector of transistor 142 and a non-inverting terminal responsive to the output of one shot 145. Input terminals of one shot 145 are connected to a timing circuit including series resistor 149 and capacitor 150, connected between the positive DC power supply voltage at terminal 105 and ground. Similar timing circuits including series connected resistor 550 and capacitor 151 and series connected resistor 551 and capacitor 552 are connected between the positive power supply voltage and ground for one shots 146 and 545.

Pulses derived from the output terminal of one shot 145 are selectively coupled under the control of slide switch 443 to an energization source to the electrodes of liquid crystal display indicator 451, to signal to the cyclist each time a heart beat occurs. Alternatively, switch 443 is activated to cause the output signal of one shot 545 to energize indicator 451, to signal to the cyclist each time his legs have turned pedals 19 one revolution.

The output signals of one shots 145, 146 and 545 are supplied to the digital computer within housing 417. If the invention is utilized in connection with a stationary bicycle, the output signals of one shots 145, 146 and 545 can be supplied to a telephone line by a suitable jack (not shown) on housing 417, for telemetering purposes. Because of the inability of a telephone line to handle very low frequency pulses, pulses derived from the output terminals of one shots 146 and 545 are converted into a DC voltage, having an amplitude proportional to the pulse rate, with such a conversion being accomplished by averaging networks (not shown) external to housing 417. Output signals derived from the averaging networks are applied as control input voltages to a pair of variable frequency oscillators (external to housing 47), which can be connected to a suitable communication link, such as a telephone line.

If the output signal of transistor 142 is noisy, whereby pulses are derived from the collector of transistor 142 more often that the minimum period between adjacent heart beats of the cyclist (0.22 seconds), as determined by the values of resistor 149 and capacitor 150, OR gate 147 blocks passage of such a noisy signal from the transistor output to the trigger input of one shot 145.

Each closure of reed switch contacts 45 and 49, each time rear wheel 24 makes a revolution and each time pedals 19 make a revolution, causes the voltages across shunt capacitors 159 and 559 to be reduced substantially to ground. Thereby, negative going pulses are established across capacitors 159 and 559, respectively connected to the positive DC voltage at terminal 105 through resistors 160 and 560. The negative going pulses, respectively developed across capacitors 159 and 559 in response to each closure of contacts 45 and 49, are coupled through inverting input terminals of OR gates 148 and 548 to trigger input terminals of one shots 146 and 545. Each such pulse is converted by one shot 146 and one shot 545 into a pulse having a predetermined amplitude and duration. To this end, one shots 146 and 545 are connected to first and second timing circuits respectively including resistor 550 in combination with capacitor 551 and resistor 552 in combination with capacitor 553.

The output terminals of one shots 146 and 545 are respectively coupled to non-inverting input terminals of OR gates 148 and 548. The connections beween the output terminals of one shots 146 and 545 and the non-inverting input terminals of OR gates 148 and 548 cause the one shots to be wried in a nonretriggerable mode. The component values associated with one shots 146 and 545 and the connections to the terminals of the one shots and to OR gates 148 and 548 are such that maximum wheel velocities of four revolutions per second and maximum pedal velocities of three revolutions per second. If there are two adjacent closures of reed switch contacts 45 in less than 0.25 seconds, the second switch closure is ignored by one shot 146 and the circuitry associated therewith because of the values of resistor 550 and capacitor 151 and the presence of OR gate 148. Similarly, if two adjacent closures of reed switch contacts 49 occur in less than 0.25 seconds, the second closure is ignored by one shot 545, by virtue of proper selection of the values for resistor 551 and capacitor 552, and as a result of the presence of OR gate 548.

Reference is now made to the system block diagram, FIGS. 10a and 10b, to provide an indication of the overall organization of the electronic circuitry included in the present invention. All of the elements illustrated in the block diagram of FIGS. 10a or 10b are located either on the surface or inside of housing 317. In addition, the circuitry of FIG. 9 is located in housing 317. The electronic circuitry illustrated in FIGS. 10a and 10b can be subdivided into a number of segments, namely: a 64 pin microcomputer 301, an eraseable programmable read-only memory 302, controller 303 for liquid crystal display 431, a 10 millisecond oscillator 304, a 2 kHz audio oscillator 305, audio selector and output circuitry 306, DC power supply 307, driver circuitry 308 for controller 303 and liquid crystal display 451, power up circuit 309, and keyboard 212.

In a preferred configuration, microcomputer 301 is a 64 pin Nippon Electric 7502 microprocessor including an internal arithmetic logic unit, accumulator, random access memory and oscillator. The arithmetic logic unit in microcomputer 301 responds to signals from timing oscillator 304, rear wheel pulses from one shot 146 (FIG. 9), pedal RPM pulses from one shot 545, heart beat signals from one shot 145, and signals from keyboard 212. The arithmetic logic unit within microcomputer 301 responds to these signals, combines them and stores them in a 4-bit accumulator for processing. Outputs of the accumulator are applied to output latches 01–08 and 01L, as well as to a random access memory and arithmetic logic unit within microcomputer 301. Data are stored in the random access memory in microcomputer 301 and sixty-four 4-bit words. The 4-bit words are conveniently grouped into four 16-word files addressed by a two-bit index register included in the microcomputer. A second 4-bit register in microcomputer 301 addresses one of the sixteen words in one of the four files within the microcomputer.

The program which controls microcomputer 301 is stored in erasable programmable read only memory 302. Memory 302 includes two separate 1K memory elements 311 and 312, each of which in a preferred embodiment is a complementary metal oxide semiconductor memory, type IM66541JG, available from Texas Instruments. Memory elements 311 and 312 are addressed in response to signals supplied by microcomputer 301 to output terminals PA0–PA3 and PC0–PC5 thereof. The addressing signals are supplied to input terminals A0–A8 of memory elements 311 and 312, with a selection of one of the memory elements being in response to opposite valued signals supplied to terminals 5 of memory elements 311 and 312 from terminal PA0 of microcomputer 301. The output at terminal PA0 is applied directly to terminal 5 of memory element 311, and to terminal 5 of memory element 312 by way of inverter 313. Memory elements 311 and 312 include parallel data output terminals D0–D7 which are applied to input terminals I0–I7 of microcomputer 301. Microcomputer 301 responds to the signals at terminals I0–I7 to control the coupling of signals between the various inputs and outputs of the microcomputer and between the elements within the microcomputer. Microcomputer 301 operates with a basic instruction cycle of ten microseconds, to provide ten thousand instructions per second, due to the values of resistor 314, connected between microcomputer terminals OSC1 and OSC2, as well as capacitor 315, which shunts terminal OSC1 to ground; terminals OSC1 and OSC2 are connected to the oscillator in the microcomputer.

Heart beat, wheel rate and pedal rate signals, respectively derive from one shots 145, 146 and 545, FIG. 9, are supplied to input terminals L2, L3 and L4 of microcomputer 301. Input terminals K1, K2, K4 and K8 of microcomputer 301 are responsive to closure of switches in keyboard 212 in response to depression of keys 201–210 and push buttons 453–460 and 560.

Key switches in keyboard 212 are arranged in a four-row by five-column matrix, with the four rows of the matrix supplying signals to input terminals K1, K2, K4 and K8 of microcomputer 301. Column leads in keyboard 212 are sequentially responsive, on a time multiplex basis, to signals supplied by microcomputer 301 to output terminals R8, R9, R10, R11 and R12 thereof.

Closure of the switch associated with start button 460 causes a pulse to be supplied to input terminal K8 of microcomputer 301 when the microcomputer is supplying a pulse to output terminal R12 thereof. The duration of the start switch closure is always sufficiently long compared to the normal operating cycle of microcomputer 301 to assure coupling of a pulse to input terminal K8, which pulse sets accumulators in microcomputer 301 to zero, and enables monitoring of other parameters by the microcomputer to be initiated. Closure of the switch associated with stop/store button 458 causes a pulse supplied by microcomputer 301 to terminal R11 to be coupled to terminal K8, to freeze the last calculated display values in memory, and enable them to be constantly supplied to liquid crystal display 431 by controller 303.

Time oscillator 304 supplies ten millisecond pulses to input terminal L8 of microcomputer 301 to enable the microcomputer to calculate elapsed exercise time, cycling speed, pedal revolution speed, fitness factor and other related parameters. Oscillator 304 includes an integrated circuit chip, in a preferred embodiment an ICM 7556 IPD chip, available from Texas Instruments. The periodicity of pulses derived from an oscillator in chip 316 is determined by the values of a timing circuit including resistors 317 and 318, in combination with capacitor 319. The series combination of resistors 317 and 318, as well as capacitor 319, is connected between a positive DC supply voltage and ground, with a tap between resistor 317 and 318 connected to terminal 13 of chip 316, and a tap between resistor 318 and capacitor 319 connected in parallel to terminals 8 and 12 of chip 316. Chip 316 has an output terminal 9 connected to input terminal L8 of microcomputer 301. The signal supplied by oscillator 304 to microcomputer 301 is counted down by frequency dividers in the microcomputer into 0.01, 0.1, 1.0 and 10 second increments, as well as into 0.1, 1.0, 10 and 100 minute increments.

Microcomputer 301 is programmed in response to signals from memory 302 to respond to the signals applied to input terminals L2, L3, K1, K2, K4, K8, L4 and L8 to calculate heart rate in beats per minute, distance traveled in miles, average speed of the distance traversed in miles per hour average revolution speed of pedals 19, in revolutions per minute, energy consumption in kilocalories, and fitness factor, as well as to determine elapsed exercise time and to selectively derive a cue signal for each desired turn of pedals 19 regardless of the bicycle gear ratio for a selected forward speed. These parameters are constantly being computed by microcomputer 301 and are selectively supplied to outputs thereof, in response to depression of keys within keyboard 212. Basically, microcomputer 301 multiplexes all of the inputs supplied to it to calculate these parameters, as well as to activate controller 303 with the various characters on program board 213. Microcomputer 301 is programmed in a conventional manner to perform these functions.

Beats per minute is determined by microcomputer 301 by combining the heart beat signal from one shot 145, as applied to terminal L2, with the output of time oscillator 304, as applied to terminal L8. Basically, microcomputer 301 responds to the signals applied to terminals L2 and L8 thereof to determine the length of time required for four beats of the heart. This time interval is divided by a constant, equal to 24,000. In other words, beats per minute is determined from:

$$\sum_{B=0}^{24,000/4} T$$

where, B equals number of heart beat signals, and T equals time in seconds.

Microcomputer 301 responds to the number of revolutions of wheel 24 signal derived from one shot 146 and the timing signals derived from oscillator 316, respectively applied to input terminals L4 and L8 of the microcomputer, as well as the wheel diameter signal, to calculate miles per hour. From the number of revolutions of wheel 24, as applied to input terminal L4, and the initial entry for wheel diameter of the subject, as derived from keyboard 212 and stored in the random access memory of microcomputer 301, and a predetermined constant relating inches to miles, the microcomputer calculates total distance in tenths of miles. From the calculation of tenths of miles, miles per hour is calculated from 60 D/T, where D equals distance in miles, and T equals time in minutes.

Microcomputer 301 responds to the signal from one shot 545 and the timing signal from oscillator 304 to provide an indication of revolutions per minute of pedals 19 in accordance with: R/T, where R equals the total number of revolutions of pedals 19, as indicated by the total number of pulses derived by one shot 545, and T equals total time in minutes.

The fitness factor of the cyclist is calculated by microcomputer 301 after cyclist 33 has exercised to his maximum ability on bicycle 11 for 12 minutes. To determine fitness factor, microcomputer 301 responds to signals supplied to input terminals L4 and L8 thereof from one shot multivibrator 146 and timing oscillator 304, as well as activation of one of gender keys 201 or 210 and numeral signals derived from keys 201–209 after display of E3, E4, E6 and E8. In response to the signal from one shot 146 and the previously keyed wheel diameter and a predetermined constant relating wheel diameter in inches to miles, distance traversed is determined by microcomputer 301. After 12 minutes of maximum capacity exercising, the fitness factor is computed in response to a pulse generated in microcomputer 301. Hence, the length of the exercise time is not a factor entering into the calculation of fitness, but is employed to determine when the fitness factor calculation should be terminated. Absolute fitness factor is calculated in response to the signal supplied to microcomputer 301 as:

$$F = \frac{Dm - a}{12} - bc + d$$

where
F = absolute fitness factor
Dm = distance traversed in meters for a 12 minute exercise
b, c and d are predetermined constants.

From the calculation of F, absolute fitness factor for a male cyclist 15 years of age or older is calculated by microcomputer 301 as:

$$F_m = \frac{eF}{g - age};$$

for a female cyclist 15 years of age or older, actual fitness is calculated by microcomputer 301 as:

$$F_f = \frac{F_m}{h}$$

where e, g, and h are predetermined constants.

Calorie consumption is computed by microcomputer 301 from exercise heart rate, as coupled to input terminal L2 of the microcomputer from one shot 145, resting heart rate, as supplied to the microcomputer from keyboard 212, heart beats per MET, which is directly proportional to fitness factor, milliliters of oxygen per minute per pound, which is directly proportional to weight in pounds of the subject, as supplied to microcomputer 301 by keyboard 212, as well as a function of sex of the subject. Microcomputer 301 computes heart beats per MET as:

$$C = jF' + m$$

where
$F'$ = fitness factor computed for the male or female cyclist, i.e., $F_m$ or $F_f$;
j and m are predetermined constants.

Computer 301 calculates milliliters of consumed oxygen for male cyclist 33 as:

$$K_m = nW = P$$

and for female cyclists as:

$$K_f = \frac{K_m}{q},$$

where W = weight of cyclist 33 and m, p and q are predetermined constants. Microprocessor 301 responds to these factors to compute calories per minute in accordance with:

$$\left(\frac{B - R}{C}\right) - vK$$

where
B = exercise heart rate in beats per minute;
R = resting heart rate in beats per minute;
K is given supra; and
v is a predetermined constant.

The equations and constants for the calculation of calories per minute are based on a so-called mixed diet of carbohydrates, fat and protein.

The calories per minute of exercise equations were evolved from a review of the literature and known research, in particular in the book "Physical Fitness and Weight Control", Charkey, Mountain Press Printing Company, 1974. It is known that the calorie consumption of the human body is directly proportional to oxygen consumption. If oxygen consumption could be directly measured, calories consumed would be related to oxygen consumption as a direct proportionality function. However, direct measurements of oxygen consumption can only be attained using sophisticated and cumbersome equipment. Thus, if it is desired to determine the calorie consumption of a subject undergoing physical activity, such as running, an indirect measurement of oxygen consumption must be made.

The hypothesis for the calorie consumption equations employed in the present invention relies upon several known phenomena. The first phenomenon is that under normal conditions there is a roughly linear relationship between oxygen uptake and heart rate during exercise for a particular subject. The roughly linear relationship has a slope that changes with the physical fitness of the subject. This is because a physically fit person is able to transport the same amount of oxygen at a lower heart rate than an unfit person. The relationship between oxygen uptake and heart rate is generally independent of sex and age, although females require higher heart rates to transport the same amount of oxygen as males. The second phenomenon relies upon the concept of METs (multiples of the metabolic need for sitting quietly) to quantify workloads of subjects undergoing exercise. The METs concept assumes that energy requirements of a subject at rest are substantially constant for a given unit of body mass. The oxygen requirement for one kilogram of body weight depends on total body weight. On average, the oxygen requirement for one kilogram of body weight is 3.5 milliliters per minute at rest, i.e., at one MET. Depending upon the source of fuel utilized by the subject (fat and/or carbohydrates), the caloric equivalent for one liter of oxygen amounts to 4700 to 5000 calories. Thus, the caloric equivalent of one MET is, on the average, 70 calories per minute per kilogram of body weight. The hourly caloric equivalent of one MET is then 1000 calories per kilogram. Assuming an exercise routine requires 10 METs, the hourly energy requirement is 10 kilocalories per kilogram, or a total of 750 kilocalories for a person with a weight of 75 kilograms.

A third factor, which has been employed and which occurs because of the linear relation between heart beat rate to oxygen uptake, is that heart rate increases are related to physical condition of the subject. This can be shown from known fitness tables as follows: heart beat rate change of eight beats per MET indicates superior physical condition; heart beat rate change of nine beats per MET indicates excellent physical condition; heart beat rate change of ten beats per MET equals good physical condition; heart beat rate change of eleven beats per MET indicates fair physical condition; heart beat rate change of twelve beats per MET indicates poor physical condition; and heart beat rate change of thirteen beats per MET indicates very poor physical condition.

A fourth factor which has been relied upon is the relationship between oxygen and calorie consumption. It has been determined that each liter of oxygen consumed is the equivalent of 4.7–5.0 kilocalories of energy. The range of 4.7–5.0 kilocalories is further defined by considering that under normal conditions athletes depend upon carbohydrates and fats as muscular energy sources. If all of the energy from a physical activity comes exclusively from carbohydrates or from fat, a person respectively uses 5.05 or 4.60 kilocalories per liter of oxygen. Most subjects, however, rely upon energy from both sources during an exercise routine. At rest, and while sprinting, most, if not all, energy comes from carbohydrates. Long duration exercise, 2 hours or more, requires energy consumption to come from body fat. However, when a person exercises aerobically for 10 to 30 minutes, 60% of the energy comes from fat and 40% comes from carbohydrates. Therefore, 4.825 calories per minute per liter of oxygen is an appropriate factor to be employed in microcomputer 301.

Because basal metabolism rates drop about ½–1% a year for each year past the age of 26 for male, and for each year past the age of 21 for female, calorie consumption in the equation is adjusted downwardly at the rate of approximately ½% for each year above 26 for males and for each year above 21 for females. Thus, microcomputer 301 also responds to the age input from keyboard 212 to calculate calories per minute of exercise. microcomputer 301 responds to the inputs to update calories per minute of exercise once a minute. Each of the updated calories per minute of exercise values is supplied to an accumulator and then is stored in the random access memory of the microcomputer, so that cyclist 33 is able to determine total calorie consumption.

The wheel and pedal pulses derived from one shots 146 and 545 are combined in microcomputer 301 with the timing signal derived from oscillator 304 to calculate gear ratio as:

$$G = \frac{QP}{W},$$

where
Q = a predetermined constant
P = pedal turning rate
W = wheel turning rate.

The calculated value of G is combined with the numerical value entered after activation of key 439 or after display of E9 for desired speed to derive a binary signal having a value in accordance with:

$$H = YGS,$$

where
Y = a predetermined constant
S = desired speed.

The desired pedal turning rate binary signal having the value H is supplied by microcomputer 301 to output terminal R7 thereof.

The binary signal at terminal R7 is converted into a series of pulses having a repetition rate equal to the necessary pedal rotation rate. The signal at terminal R7 is supplied to digital to analog converter 601 which derives a d.c. level having an amplitude proportional to necessary pedal rate. The d.c. level derived from converter 601 is supplied to a frequency control input of voltage controlled, variable frequency oscillator 602. Oscillator 602 generates a series of pulses having a frequency determined by the signal amplitude applied to it by converter 602. The pulses from oscillator 602 are selectively combined with a 2 KHz tone and gated to piezoelectric crystal 335, to generate an aural cue signal for each turn of pedals 20 necessary to achieve the desired speed as described infra.

Microcomputer 301 has four outputs R0–R3 and O1–O8 which drive eight inputs of liquid crystal display controller 303. In a preferred embodiment, display controller 303 is an integrated circuit element, with a nomenclature ICM 7211 AIPL. Display controller 303 responds to the signals applied by microcomputer 301 to input terminals D1–D4 and DS1–DS4 to energize three liquid crystal display characters 321, 322 and 323 in liquid crystal display 431. Each of characters 321, 322 and 323 includes seven segments, arranged in a straight line so that when all segments of a character are activated, the character appears to be the numeral 8. Segments of characters 321, 322 and 323 are selectively activated in response to signals supplied to input terminals D1–D4 and DSL–DS4 of controller 303 to enable display of 16 characters, viz: 0, 1, 2, 3, 4, 5, 6, 7, 8, 9, H, E, L and P, as well as a blank. Controller 303 includes, internally thereof, a self-contained resistance capacitance oscillator, a divider chain, a backplane driver, and 28 segment outputs, for four different characters. The 28 segment outputs provide a zero DC component signal necessary for a long display life for the liquid crystals in display 31. Controller 303 is supplied with true binary signals from microcomputer terminals O1, O2, O4 and O8. The data from microcomputer 301 are strobed into controller 303 under the control of outputs R0–R3 of microcomputer 301. The least significant digit output of controller 303 is strobed under the control of the signal at output terminal R2 of microcomputer 301, while the most significant digit of controller 303 is strobed under control of the signal at terminal R3. Only three of the available eight segments are used in the least significant bit position of the output of controller 303 to control annunciators associated with time key 457, calorie key 455, miles per hour key 454, distance key 453, and pedal rpm key 560.

Controller 303 includes a further output terminal BP which is energized in response to a predetermined state of the segment supplied by terminals O1, O2, O4 and O8 to controller 303 to enable the gates of gate array 308 simultaneously by virtue of a parallel input to the gates from terminal BP. Four exclusive OR gates 325–329 are included in gate array 308. Gate 325, responsive to a signal at output terminal OSL of microcomputer 301, includes an output terminal connected to drive decimal point 330 in liquid crystal display 431, which decimal point is positioned between characters 321 and 322. Gate 326, connected to output terminal R5 of microcomputer 301, when biased by the signal at terminal BP of controller 303, drives an annunciator associated with distance key 453. Gate 327 has an input terminal responsive to the signal at output terminal R4 of microcomputer 301 and an output terminal connected to drive an annunciator associated with beats per minute key 359. Exclusive OR gate 328 has an input responsive to one shot 145 and an output which selectively drives annunciator 571 associated with LCD 451. Annunciator 571 is also selectively responsive to the output signal of one shot 545.

In response to slide switch 433 being in the audio or mute position, the contact of switch 553 couples the output of gate 328 to annunciator 571, whereby LCD 451 is activated for each heart beat of cyclist. In response to switch 433 being in the RPM position, the contact of switch 553 couples the output of one shot 545 to annunciator 571, whereby LCD 451 is activated for each turn of pedals 19. Thereby LCD 451 is activated for each heart beat pulse derived from one shot 145 or in response to each pedal revolution pulse derived from one shot 145. The annunciators responsive to the outputs of exclusive OR gates 325–328 for the time, calories, and miles per hour outputs of controller 303 are not shown but are conventional and obvious to those skilled in the art; for example, the annunciator associated with the time, calorie, beats per minute, miles per hour and mile outputs of controller 303 and gates 325–328 are connected in series with the switches in keyboard 212 with which they are associated.

The aural indications derived from the speaker behind screen 452 are selectively derived. The aural signal has a tone at a fixed frequency of 2 kiloHertz, as derived from audio oscillator 305. Audio oscillator 305 is preferably an integrated circuit chip, type ICM 7556 IPD, having a frequency determined by the values of resistors 331 and 332, connected in series with each other and capacitor 333. The series circuit including resistors 331 and 332, as well as capacitor 333, is connected between a plus DC power supply voltage and ground. A tap between resistors 331 and 332 is connected to input terminal 1 of chip 330; a tap between resistor 332 and capacitor 333 is connected in parallel to input terminals 2 and 6 of chip 330. Chip 330 is selectively activated in response to an output signal of microcomputer 301 at terminal R13.

The audio output signal of oscillator chip 330, at terminal 5 thereof, is selectively gated to piezo electric audio indicator 335 which drives the speaker behind grill 452 in response to the heart beat output signal of one shot 145, the pulses from oscillator 602, and the output signals at terminals R14 and R15 of microcomputer 301. The signals are combined in an array of gates including NAND gates 336, 337, 338, 603, 604 and 605 and OR gate 606 each of which includes two input terminals. The two input terminals of NAND gate 336 are respectively responsive to the output signal of oscillator chip 330, at terminal 5 thereof, and the output of microcomputer 301 at terminal R14, which also drives one of the inputs of NAND gate 337. The remaining input of NAND gate 337 is responsive to the heart beat output signal of one shot 145. Gate 603 is responsive to the pulse output of oscillator 602 and the signal at output terminal R15 of microcomputer 301, while gate 604 is responsive to the signal at terminal R15 and the 2 KHz tone derived from oscillator 305. Output signals of NAND gates 336 and 337 are combined in NAND gate 338, while the output signals of NAND gates 603 and 604 are combined in NAND gate 605. Non zero outputs, derived on a mutually exclusive basis from gates 338 and 605, are supplied to OR gate 606, having an output which is DC coupled to the base of NPN transistor 339, connected in the common emitter mode, so that piezo electric crystal 335 is connected between a positive DC power supply voltage and the transistor collector.

Gates 336–338 and 603–606 are connected to be responsive to the output signals of voltage controlled oscillator 602, one shot 145, integrated circuit chip 330 and the signals at terminals R14 and R15 of microcomputer 301, and terminal 4 of chip 330 is responsive to the signal at terminal R13 of microcomputer 301, so that: (1) no audio signal is derived from piezo electric crystal 335 in response to binary zeros being derived at output terminals R13, R14 and R15 of microcomputer 301; (2) a 2 KHz audio output signal is derived from crystal 335 in response to each heart beat pulse derived from one shot 145, when binary one, zero and zero signals are respectively derived from terminals R13, R14 and R15 of microcomputer 301; (3) a continuous two KHz audio output signal is derived from crystal 335 in response to binary one, one and zero signals being respectively derived from output terminals R13, R14 and R15 of microcomputer 301; and (4) 2 KHz audio output pulses are derived from crystal 335 at a variable rate, once for each desired turn of pedals 20, in response to binary one, zero and one signals at output terminals R13, R14 and R15 of microcomputer 301.

DC power is supplied to the circuit components illustrated in FIGS. 10a and 10b by a power supply network including three series AA dry cells 341, each of which has a voltage of 1.5 volts. Dry cells 341 are selectively connected to the circuitry through switch contacts 342 which are responsive to movement of toggle switch 214, FIG. 5a. The voltage supplied through switch contacts 342 is regulated by back biased diode 343, across which is connected the parallel combinations of light switch 344 and light emitting diode 345, which corresponds with lamp 461, on housing 417. For the power down situation, the voltage developed across diode 343 is selectively applied by switch contact 346, when the device is not in the power down state, to all of the active circuit elements of FIGS. 9, 10a and 10b, except microcomputer 301. Of course, memory elements 311 and 312 remain programmed even though they are not supplied with power by way of switch 346 because they are read only memories. Power is continuously applied to microcomputer 301, regardless of the position of switch 346, as long as switch 342 is closed, by virtue of the connection of switch contact 342 to terminal BATT of microcomputer 301. Thereby, the random access memory within microcomputer 301 stores data during the power down mode, to minimize the drain on batteries 341; with switch 346 opened and switch 342 closed, so power is applied only to microcomputer 301, the drain from dry cells 341 is approximately 1 microampere.

Power up circuit 309 sets the random access memory of computer 301 to a predetermined programmed position for initiation and execution of the program algorithm stored in the read only memory 302. Power up circuit 309 also includes switch 351, which is responsive to depression of clear entry button 216. Power up circuit 309 includes back biased diode 352, shunted by resistor 353. The parallel combination of diode 352 and resistor 353 is connected by capacitor 354 to terminal 5 of microcomputer 301. Capacitor 354 is selectively short circuited by closure of switch contacts 351, which also sets microcomputer 301 to the predetermined initial program position for execution of the program algorithm stored in read only memory 302.

While there have been described and illustrated several specific embodiments of the invention, it will be clear that variations in the details of the embodiments specifically illustrated and described may be made without departing from the true spirit and scope of the invention as defined in the appended claims. For example, the invention can be used by physicians or cyclists in connection with a conventional EKG chart recorder responsive to the EKG signal derived from amplifier 103, FIG. 9. The invention can be utilized with any self-propelled cycle device, whether it be a stationary device or a moving device. Certain aspects of the invention can be utilized with other self-propelled devices requiring considerable expenditure of energy by an athlete, such as rowing machines, row boats, kayaks, and the like.

What is claimed is:

1. A device for enabling the speed of a bicycle wheel having spokes to be determined comprising a bicycle reflector, a housing for carrying the reflector, means for mounting the housing on the spokes so the reflector is substantially broadside to the direction of wheel travel, and a permanent magnet carried by the housing in a position enabling magnetic flux to be coupled from the permanent magnet to a magnetic flux sensitive transducer mounted on a part of the bicycle stationary relative to the spokes and the reflector to be seen by viewers broadside of the wheel.

2. A device for enabling the speed of a bicycle wheel having spokes to be determined comprising a bicycle reflector, a first housing for carrying the reflector, means for mounting the first housing on the spokes so the reflector is substantially broadside to the direction of wheel travel, a magnetic flux transducer, a second housing for the transducer, means for mounting the second housing on a part of the bicycle stationary with respect to the wheel, and a permanent magnet carried by the first housing in a position enabling magnetic flux to be coupled from the permanent magnet to the transducer and the reflector to be seen by viewers broadside of the wheel.

3. The device of claim 2 wherein the transducer includes a reed switch with contacts responsive to the magnetic flux.

4. The device of claim 2 or 3 wherein the second housing mounting means includes means for enabling the second housing to be selectively secured to and removed from the bicycle part.

5. Apparatus for testing the physical condition of a cyclist comprising means adapted to be mounted on the subject for monitoring and deriving a first signal indicative of heart activity of the subject, means adapted to be mounted on a cycle for deriving a second signal indicative of distance traversed by the cycle during testing, input means for deriving at least one signal indicative of a predetermined physiological parameter of the subject, a clock source for deriving a timing signal during testing of the cyclist, computer means responsive to the first, second, predetermined physiological parameter and timing signals for calculating deriving a signal indicative of physical activity of the cyclist being tested, and indicator means responsive to the physical activity signal.

6. The apparatus of claim 5 wherein the first signal deriving means includes means for monitoring the number of heart beats of the subject.

7. The apparatus of claim 6 wherein the computer means responds to the second signal and the clock source for deriving another signal indicative of the speed of the bicycle during testing.

8. The apparatus of claim 5 wherein the computer means responds to the second signal and the clock source for deriving another signal indicative of the speed of the bicycle during testing.

9. The apparatus of claim 5 or 8 wherein the bicycle has a wheel with spokes, and second signal deriving means includes a bicycle reflector, a first housing for carrying the reflector, means for mounting the first housing on the spokes so the reflector is substantially broadside to the direction of wheel travel, and a permanent magnet carried by the first housing in a position enabling magnetic flux to be coupled from the permanent magnet to a magnetic flux sensitive transducer mounted on a part of the bicycle stationary relative to the spokes and the reflector to be seen by viewers broadside of the wheel.

10. The apparatus of claim 5, 6, 7 or 8 wherein the bicycle includes a sprocket assembly and further including means for deriving a pulse for each revolution of the sprocket assembly, the computer responding to the pulses and the clock source for calculating deriving a signal indicative of number of sprocket assembly turns per unit length of time.

11. The apparatus of claim 10 wherein the pulse deriving means includes a permanent magnet mounted on the sprocket assembly, and a magnetic flux sensor mounted on a part of the bicycle about which the sprocket assembly turns and positioned to respond to magnetic flux variations resulting from the permanent magnet turning with the sprocket assembly.

12. The apparatus of claim 10 wherein the pulse deriving means includes a permanent magnet mounted on the sprocket assembly, and a reed switch having contacts, the reed switch being mounted on a part of the bicycle about which the sprocket assembly turns and positioned so the contacts respond to magnetic flux variations resulting from the permanent magnet turning with the sprocket assembly.

13. Apparatus for testing the physical condition of a subject riding a vehicle propelled by the subject comprising means adapted to be mounted on the subject for monitoring and deriving a first signal indicative of heart activity of the subject, means adapted to be mounted on the vehicle for deriving a second signal associated with distance traversed by the subject during testing, a portable electronic instrument housing, means for coupling said first and second signals to terminals on the instrument housing, said housing including: (a) a keyboard for enabling signals to be derived indicative of numerical quantities associated with plural physiological parameters of the subject, (b) a clock source for deriving timing signals, (c) digital computer means responsive to the first, second, timing and keyboard signals for calculating plural digital output signals indicative of different physical activities of the tested subject, (d) visual digital indicator means, (e) plural key switches, each associated with a different one of the physical activities, and (f) means responsive to activation of the plural key switches for selectively coupling different ones of the plural output signals to the visual indicator means so only one of the output signals is supplied to the indicator means at a time.

14. The apparatus of claim 13 wherein the first signal deriving means includes means for monitoring the number of heart beats of the subject.

15. The apparatus of claim 14 wherein the vehicle is a bicycle and the computer means responds to the second signal and the clock source for deriving another signal indicative of the speed of the bicycle during testing.

16. The apparatus of claim 13 wherein the vehicle is a bicycle and the computer means responds to the second signal and the clock source for deriving another signal indicative of the speed of the bicycle during testing.

17. The apparatus of claim 13 or 16 wherein the vehicle is a bicycle having a wheel with spokes, said second signal deriving means including a bicycle reflector, a first housing for carrying the reflector, means for mounting the first housing on the spokes so the reflector is substantially broadside to the direction of wheel travel, and a permanent magnet carried by the first housing in a position enabling magnetic flux to be coupled from the permanent magnet to a magnetic flux sensitive transducer mounted on a part of the bicycle stationary relative to the spokes and the reflector to be seen by viewers broadside of the wheel.

18. The apparatus of claim 13, 14 or 15 wherein the vehicle is a bicycle including a sprocket assembly and further including means for calculating a pulse for each revolution of the sprocket assembly, the computer responding to the pulses and the clock source for calculating a signal indicative of number of sprocket assembly turns per unit length of time.

19. The apparatus of claim 18 wherein the pulse deriving means includes a permanent magnet mounted on the sprocket assembly, and a magnetic flux sensor mounted on a part of the bicycle about which the sprocket assembly turns and positioned to respond to magnetic flux variations resulting from the permanent magnet turning with the sprocket assembly.

20. The apparatus of claim 8 wherein the pulse deriving means includes a permanent magnet mounted on the sprocket assembly, and a reed switch having contact, the reed switch being mounted on a part of the bicycle about which the sprocket assembly turns and positioned so the contacts respond to magnetic flux variations resulting from the permanent magnet turning with the sprocket assembly.

21. The apparatus of claim 13 wherein the vehicle is a multigear cycle, means for deriving a cueing signal to assist the cyclist in maintaining a desired constant forward speed regardless of gear ratio, said cueing signal deriving means including transducer means for deriving third and fourth signals respectively indicative of pedal and wheel turning speeds, said computer means being responsive to the third and fourth signals and an indication of the desired, constant forward speed for calculating deriving the cueing signal.

22. The apparatus of claim 21 wherein the transducer means includes means for deriving a pulse each time the wheel turns.

23. The apparatus of claim 21 or 22 wherein the transducer means includes means for deriving a pulse each time the pedal turns.

24. The apparatus of claim 23 wherein the cueing signal is an aural pulse derived at a rate of once for each desired pedal turn.

25. The apparatus of claim 21 or 22 wherein the cueing signal is an aural pulse derived at a rate of once for each desired pedal turn.

26. Apparatus for supplying cueing signals to a cyclist of a multigear cycle propelled by turning of pedals, the cueing signal being designed to assist the cyclist in maintaining a desired, constant forward speed regardless of gear ratio, comprising transducer means for deriving first and second signals respectively indicative of pedal and wheel turning speeds, and means for combining first and second signals and an indication of the desired, constant forward speed for calculating the frequency of a cueing signal and for deriving a cueing signal at the computed frequency.

27. The apparatus of claim 26 wherein the transducer means includes means for deriving a pulse each time the wheel turns.

28. The apparatus of claim 26 or 27 wherein the transducer means includes means for deriving a pulse each time the pedal turns.

29. The apparatus of claim 28 wherein the cueing signal is an aural pulse derived at a rate of once for each desired pedal turn.

30. The apparatus of claim 26 or 27 wherein the cueing signal is an aural pulse derived at a rate of once for each desired pedal turn.

* * * * *